(12) United States Patent
Dahiyat et al.

(10) Patent No.: US 7,315,786 B2
(45) Date of Patent: *Jan. 1, 2008

(54) PROTEIN DESIGN AUTOMATION FOR PROTEIN LIBRARIES

(75) Inventors: Bassil I. Dahiyat, Los Angeles, CA (US); Jörg Bentzien, Pasadena, CA (US); Klaus M. Fiebig, Frankfurt (DE); Robert J. Hayes, Pasadena, CA (US)

(73) Assignee: Xencor, Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/927,790

(22) Filed: Aug. 10, 2001

(65) Prior Publication Data

US 2002/0090648 A1   Jul. 11, 2002

Related U.S. Application Data

(63) Continuation of application No. 09/782,004, filed on Feb. 12, 2001, and a continuation of application No. 09/419,351, filed on Oct. 15, 1999, now Pat. No. 6,403,312.

(60) Provisional application No. 60/197,851, filed on Apr. 14, 2000, provisional application No. 60/186,904, filed on Mar. 3, 2000, provisional application No. 60/181,630, filed on Feb. 10, 2000, provisional application No. 60/158,700, filed on Oct. 8, 1999, provisional application No. 60/104,612, filed on Oct. 16, 1998.

(51) Int. Cl.
*G01N 31/00* (2006.01)
*G06F 17/00* (2006.01)

(52) U.S. Cl. .......................... 702/19; 702/27; 706/45; 706/46

(58) Field of Classification Search ................ 435/7.1, 435/5, 4; 530/350; 702/19, 27; 706/45, 706/46

See application file for complete search history.

(56) References Cited

U.S. PATENT DOCUMENTS

| | | | |
|---|---|---|---|
| 4,939,666 A | 7/1990 | Hardman | |
| 5,241,470 A | 8/1993 | Lee et al. | |
| 5,265,030 A | 11/1993 | Skolnick et al. | |
| 5,436,850 A | 7/1995 | Eisenberg et al. | |
| 5,527,681 A | 6/1996 | Holmes | 435/6 |
| 5,878,373 A | 3/1999 | Cohen et al. | |
| 6,188,965 B1 | 2/2001 | Mayo et al. | |
| 6,269,312 B1 | 7/2001 | Mayo et al. | |
| 6,403,312 B1* | 6/2002 | Dahiyat et al. | 435/6 |
| 2002/0048772 A1 | 4/2002 | Dahiyat et al. | |
| 2002/0090648 A1 | 7/2002 | Dahiyat et al. | |
| 2004/0043429 A1 | 3/2004 | Dahiyat et al. | |
| 2004/0043430 A1 | 3/2004 | Dahiyat et al. | |

FOREIGN PATENT DOCUMENTS

| | | |
|---|---|---|
| EP | 0549107 A | 6/1993 |
| WO | 95/22625 | 8/1995 |
| WO | WO98/05765 A | 2/1998 |
| WO | 98/32845 | 7/1998 |
| WO | WO98/32845 A | 7/1998 |
| WO | 98/47089 | 10/1998 |
| WO | WO98/47089 A1 | 10/1998 |
| WO | 00/23564 | 4/2000 |
| WO | WO 00/40715 A | 7/2000 |
| WO | 00/68396 | 11/2000 |
| WO | WO 01/37147 A | 5/2001 |
| WO | WO 01/39098 A | 5/2001 |
| WO | WO 01/61344 A | 8/2001 |
| WO | WO 03/006154 A | 1/2003 |
| WO | WO94/16090 A | 7/2004 |

OTHER PUBLICATIONS

Shakhnovich, E. Folding and Design, 1998, 3, R45-R58.*
Brenner and Berry, A., et al., "A quantitative methodology for the de novo design of proteins", Protein Sci. 3:1871-1882 (Oct. 1994).
Borman, "Proteins to Order," Chemical and Engineering Newsletter (C&EN) Oct. 6, 1997, 9-10 (1997).
Bowie, J.U., et al., "Deciphering the Message in Protein Sequences: Tolerance to Amino Acid Substitutions", Science vol. 247:1306-1310 (Mar. 1990).
Brooks et al., "CHARMM: A Program for Macromolecular Energy, Minimization, and Dynamics Calculations," J. of Computational Chemistry, 4(2):187-217 (1983).
Connolly, M.L., "Solvent-Accessible Surfaces of Proteins and Nucleic Acids", Science vol. 221(4612):709-713 (Aug. 1983).
Cornell et al., "A Second Generation Force Field for the Simulation of Proteins, Nucleic Acids, and Organic Molecules," J. Am. Chem. Soc., 117:5179-5197 (1995).
Dahiyat, B.I., et al., "Automated design of the surface positions of protein helices", Protein Science 6:1333-1337 (Jun. 1997).
Dahiyat et al., "Protein design automation," Caltech Biology Annual Report, 172 (1995).
Dahiyat et al., "Protein Design Automation," Meeting Abstract; Protein Science vol. 4, Suppl. 2, 83 (1995).
Dahiyat et al., "Protein Design Automation," Poster Sessions, Protein Science vol. 5, Suppl. 1, 22-23 (1996).
Dahiyat et al., "Probing the Role of Specificity in Protein Design," Caltech Biology Annual Report, 160-161 (1996).
Dahiyat, B.I., et al., "First fully automatic design of a protein achieved by Caltech scientists", new press release (Oct. 1997).
Dalal, S., et al., "Protein alchemy: Changing .beta.-sheet into .alpha.-helix", Nature Struc. Biol. vol. 4(7):548-552 (Jul. 1997).
DeGrado, W., "Proteins from Scratch," Science, 278:80-81 (1997).
Desjarlais et al., "New strategies in protein design," Current Opinion in Biotechnology :460-466 (1995).

(Continued)

*Primary Examiner*—Michael Borin
(74) *Attorney, Agent, or Firm*—Morgan Lewis & Bockius LLP; Robin M. Silva, Esq.

(57) ABSTRACT

The invention relates to the use of protein design automation (P DA) to generate computationally prescreened secondary libraries of proteins, and to methods and compositions utilizing the libraries.

18 Claims, 7 Drawing Sheets

OTHER PUBLICATIONS

Desmet, J., et al., "The 'Dead End Elimination' Theorem: A New Approach to the Side Chain Packing Protein", from "The Protein Folding Problem and Tertiary Structure Prediction" Ch.10:1-49 (1994).

Desmet, J., et al., "The dead-end elimination theorem and its use in protein side-chain positioning", Nature vol. 356:539-542 (Apr. 1992).

Desmet et al., "Theoretical and Algorithmical Optimization of the Dead-End Elmination Theorem," Proceedings of the Pacific Symposium on Biocomputing '97, 122-133 (1997).

Dunbrack Jr., R.L., et al., "Conformational analysis of the backbone-dependent rotamer preferences of protein sidechains", Struc. Biol. vol. 1(5):334-340 (May 1994).

Eisenberg, D., et al., "Solvation energy in protein folding and binding", Nature vol. 319:199-203 (Jan. 1986).

Goldstein, R.F., "Efficient Rotamer Elimination Applied to Protein Side-Chains and Related Spin Glasses", Biophys. Jour. vol. 66:1335-1340 (May 1994).

Gordon et al. "Energy functions for protein design," Curr. Opinion in Struct. Biol., 9:509-513 (1999).

Harbury et al., "High-Resolution Protein Design with Backbone Freedom," Science, 282:1462-1467 (1998).

Hellinga, H.W., "Rational protein design: Combining theory and experiment", Proc. Natl. Acad. Sci, USA vol. 94:10015-10017 (Sep. 1997).

Holmes, "First-ever designer protein fits like a glove," New Scientist, IPC Magazines Limited, Oct. 11, 1997 (1997).

Hurley et al., "Design and Structural Analysis of Alternative Hydrophobic Core Packing Arrangements in Bacteriophage T4 Lysozyme," J. Mol. Biol., 224:1143-1159(1992).

Koehl et al., "De Novo Protein Design. I. In Search of Stability and Specificity," J. Mol. Biol., 293:1161-1181 (1999).

Kortemme et al., "Design of a 20-Amino Acid, Three-Stranded $\beta$-Sheet Protein," Science, 281:253-256 (1988).

Lasters et al., "Enhanced dead-end elimination in the search for the global minimum energy conformation of a collection of protein side chains," 1995, Protein Engineering, vol. 8, No. 8, pp. 815-822.

Lasters, I., et al., "Dead-End Based Modeling Tools to Explore the Sequence Space That is Compatible with a Given Scaffold", Jour. of Protein Chem. vol. 16(5):449-452 (Jul. 1997).

Lazar et al., "De novo design of the hydrophobic core of ubiquitin," Protein Science 6:1167-1178 (1997).

Lee et al., "Accurate prediction of the stability and activity effects of site-directed mutagenesis on a protein core," Nature, 352:448-451 (1991).

Lim et al., "The crystal structure of a mutant protein with altered but improved hydrophobic core packing," Proc Natl Acad Sci U S A. Jan. 4, 1994;91(1):423-7.

Mayo et al., "DREIDING: A Generic Force Field for Molecular Simulations," J. Phys. Chem., 94:8897-8909 (1990).

Minor Jr., D.L., "Measurement of the .beta.-sheet-forming propensities of amino acids", Nature vol. 367:660-663 (Feb. 1994).

Munoz, V., et al., "Helix design, prediction and stability", Curr. Opin. in Biotech. 6:382-386 (Aug. 1995).

Munoz, V., et al., "Intrinsic Secondary Structure Propensities of the Amino Acids, Using Statistical phi-psi Matrices: Comparison with Experimental Scales", Proteins 20:301-311 (1994).

Munoz, V., et al., "Analysis of the effect of local interactions on protein stability", Folding & Design 1(3):167-178 (Apr. 1996).

Pabo, C., "Designing proteins and peptides", Nature vol. 301:200 (Jan. 1983).

Padmanabhan, S., et al., "Relative helix-forming tendencies of nonpolar amino acids", Nature vol. 344:268-270 (Mar. 1990).

Ponder, J.W., et al., "Use of Packing Criteria in the Enumeration of Allowed Sequences for Different Structural Classes", release by Acad. Press Inc. (London) Ltd. pp. 775-791(1987).

Rappe et al., "Charge Equilibration for Molecular Dynamics Simulations," J. Phys. Chem., 95:3358-3363 (1991).

Regan, L., "Helix is a helix is a helix?", Proc. Natl. Acad. Sci. USA vol. 94:2796-2797 (Apr. 1997).

Smith, C.K., et al., "Guidelines for Protein Design: The Energetics of .beta. Sheet Side Chain Interactions", Science vol. 270:980-982 (Nov. 1995).

Stickle et al., "Hydrogen Bonding in Globular Proteins," (1992) Journal of Molecular Biology, vol. 226, pp. 1143-1159.

Sun, S., et al., "Designing amino acid sequences to fold with good hydrophobic cores", Protein Eng. vol. 8(12):1205-1213 (1995).

Tuffery et al., "A New Approach to the Rapid Determination of Protein Side Chain Conformations," J. of Biomolecular Struct. & Dynamics, 8(6):1267-1289 (1991).

van Gunsteren et al., "Prediction of the Activity and Stability Effects of Site-directed Mutagenesis on a Protein Core," J. Mol. Biol., 227:389-395 (1992).

Villegas et al., "Stabilization of proteins by rational design of alpha.-helix stability using helix/coil transition theory," Folding & Design, 1(1):29-34 (1995).

Wesson et al., "Atomic solvation parameters applied to molecular dynamics of proteins in solution," Protein Science, 1:227-235 (1992).

Wilson et al. "Computational Method for the Design of Enzymes with Altered Substrate Specificity," J. Mol. Biol. (1991) 220,495-506.

Bowie et al., "A Method to Identify Protein Sequences that Fold into a Known Three-Dimensional Structure," Science 253:164-170 (1991).

Dahiyat and Mayo, "Protein Design automation", Protein Science 5:895-903 (1996).

Dahiyat and Mayo, "De Novo Protein Design: Fully Automated Sequence Selection," Science 278:82-87 (1997).

Desjarlais and Handel, "De novo design of the hydrophobic cores of proteins", Protein Science 4:2006-2018 (1995).

Harbury et al., "Repacking protein cores with backbone freedom: Structure prediction for coiled coils", Proc. Natl. Acad. Sci. USA 92:8408-8412 (1995).

Kono and Doi, "Energy Minimization Method Using Automata Network for Sequence and Side-Chain Conformation Prediction From Given Backbone Geometry", Proteins: Structure, Function and Genetics 19:244-255 (1994).

Hellinga, et al., "Optimal sequence selection in proteins of known structure by simulated evolution", Proc. Natl. Acad. Sci., USA vol. 91:5803-5807 (1994).

Jones, "De novo protein design using pairwise potentials and a genetic algorith", Protein Science 3:567-574 (1994).

Lam et al., "Application of combinatorial library methods in cancer research and drug discovery," Anti-Cancer Drug Design 12:145-167 (1997).

Gallop et al., "Applications of Combinatorial Technologies to Drug Discovery. 1. Background and Peptide Combinatorial Libraries," J Med Chem 37(9):1233-1251 (Apr. 1994).

Fechteler T, et al., "Prediction of protein three-dimensional structures in insertion and deletion regions: a procedure for searching data bases of representative protein fragments using geometric scoring criteria." J Mol Biol. Oct. 13, 1995;253(1):114-31.

Malakauskas SM, and Mayo SL. "Design, structure and stability of a hyperthermophilic protein variant." Nat Struct Biol. Jun. 1998;5(6):470-5.

Wallace AC, et al., "Derivation of 3D coordinate templates for searching structural databases: application to Ser-His-Asp catalytic triads in the serine proteinases and lipases." Protein Sci. Jun. 1996;5(6):1001-13.

Hellinga HW, and Richards FM. "Construction of new ligand binding sites in proteins of known structure. I. Computer-aided modeling sites with predefined geometry." J Mol Biol. Dec. 5, 1991;222(3):763-85.

Wodak, S.J., "Analytical approximation to the accessible surface area of proteins", Proc. Natl. Acad. Sci. USA vol. 77(4):1736-1740 (Apr. 1980).

Cojee et al. "Seamless gene engineering using RNA- and DNA-overhang cloninig" Nature Biotechnology, vol. 18, (2000) pp. 1087-0156.

Gal J. et al. "Directional Cloning of Native PCR Products with Performed Sticky Ends" *Mol. Gen. Genet.* vol. 260, No. 6, (1999), pp. 569-573.

Koehl P. et al., "De novo protein design I. in search of stability and specificity" *J.Mol.Biol.,* vol. 293, No. 5, (1999) pp. 1161-1181.

Wernisch L. et al. "Automatic protein design with all atom force-fields by exact and heuristic optimization" *J. Mol. Biol.* vol. 301, No. 3, (2000), pp. 713-736.

Dayhoff, M. "Establishing Homologies in Protein Sequences" (1983) *Methods in Enzymology,* vol. 91, 524-545.

* cited by examiner

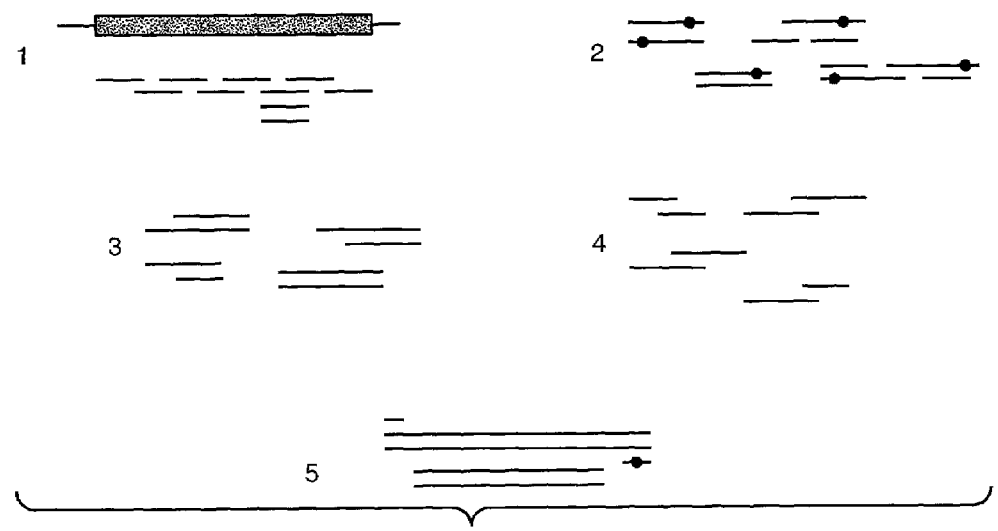
FIG._1
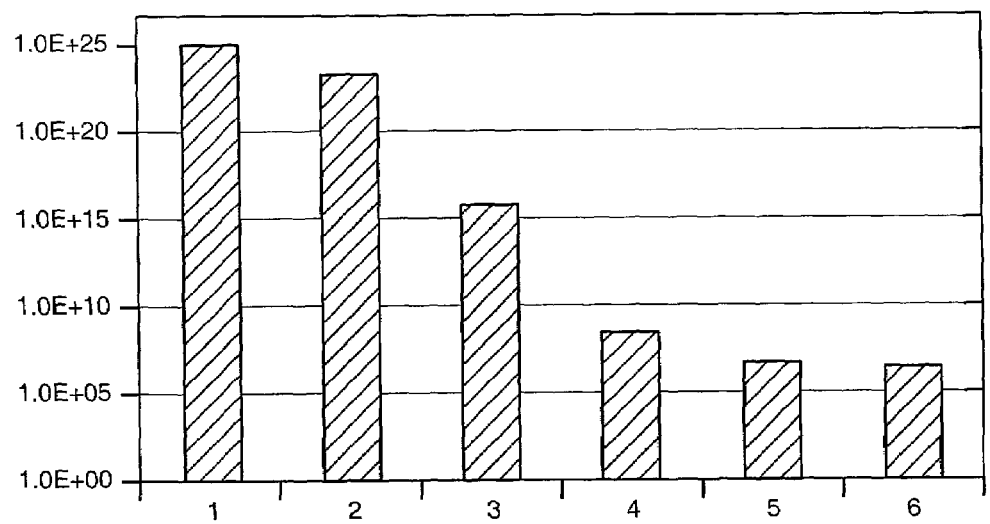
FIG._2

FIG._3
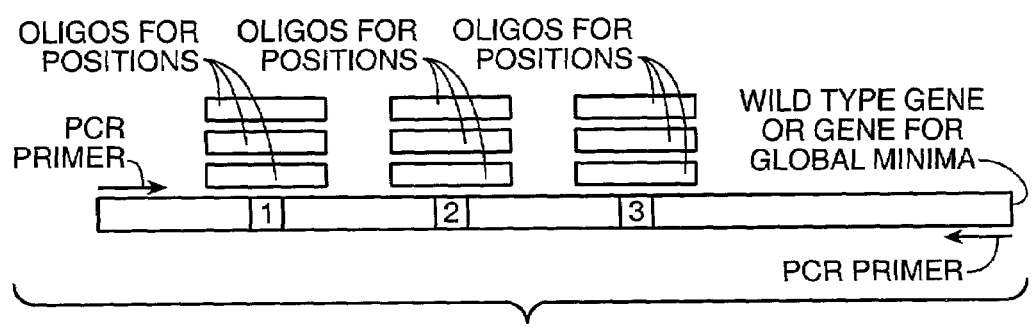
FIG._5

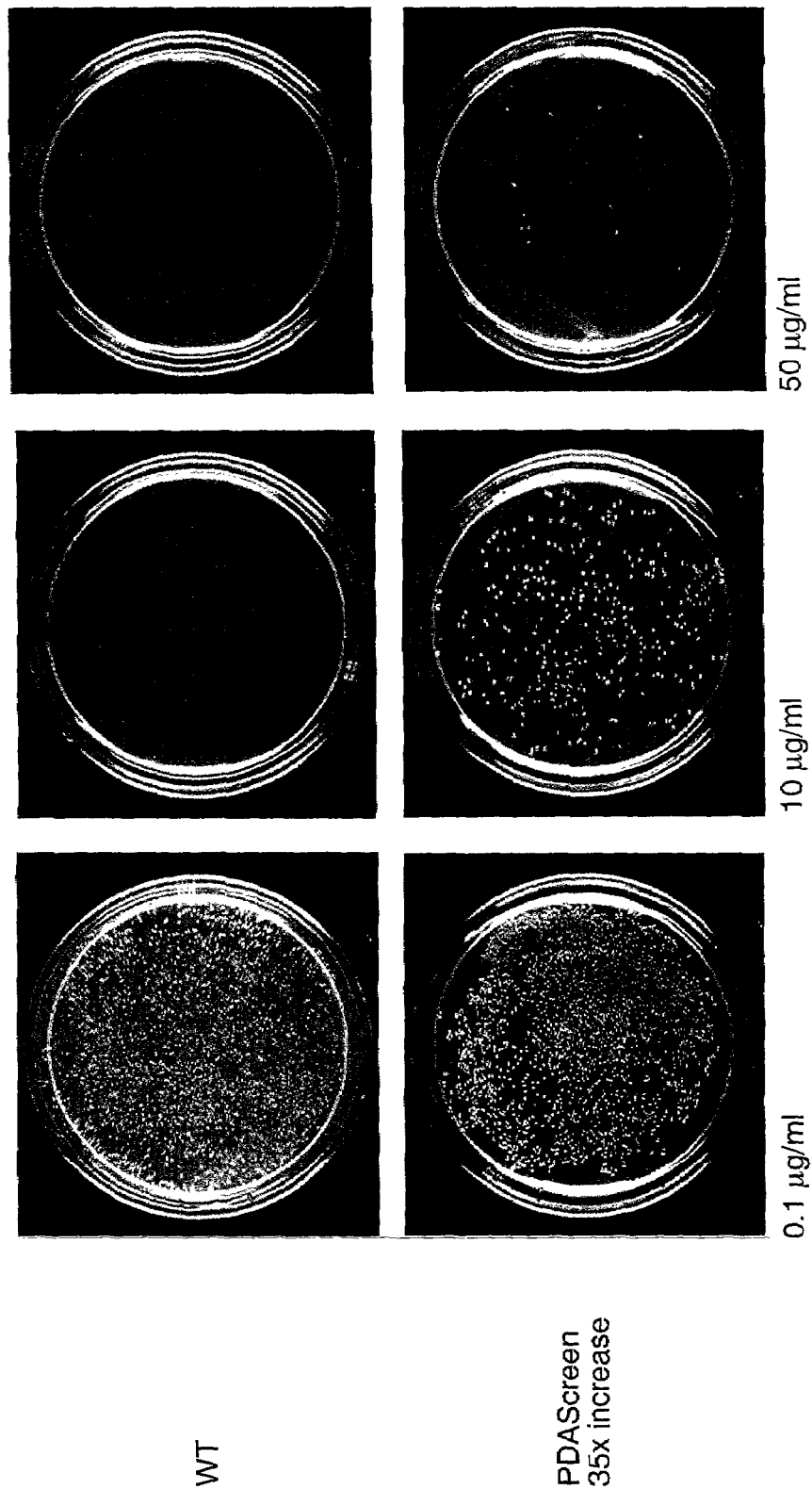
FIG._4

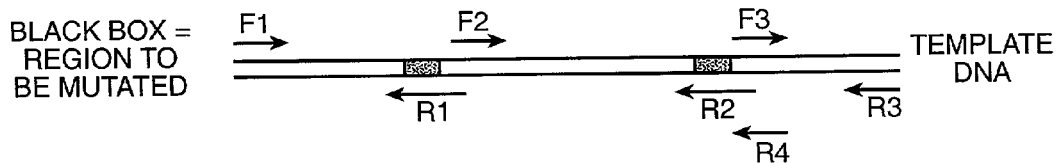
BLACK BOX = REGION TO BE MUTATED
TEMPLATE DNA
STEP 1: SET UP 3 PCR REACTIONS:
PRODUCTS:
TUBE 1:
TUBE 2:
TUBE 3:
STEP 2: SET UP PCR REACTION WITH PRODUCTS OF TUBE 1 + PRODUCTS TUBE 2 + F1 + R4.
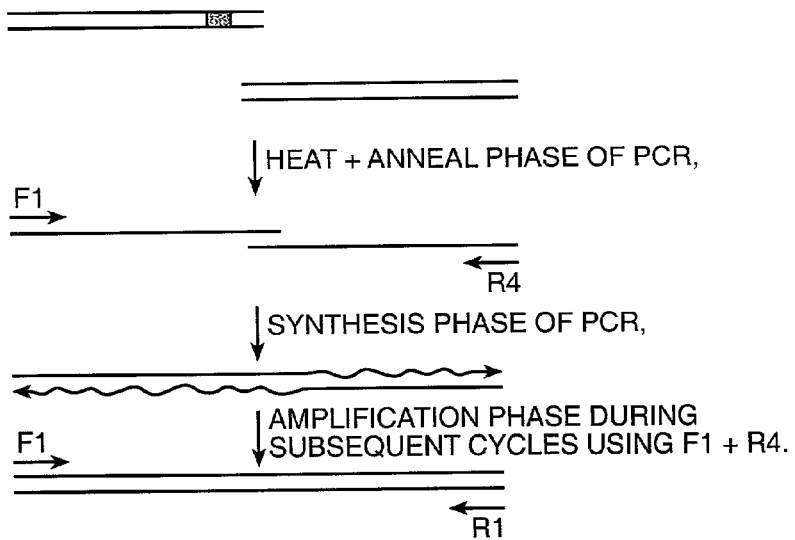
STEP 3: REPEAT STEP 2 USING PRODUCT FROM STEP 2 + PRODUCT FROM STEP 1, TUBE 3 + PRIMERS F1 + R3.
FIG._6

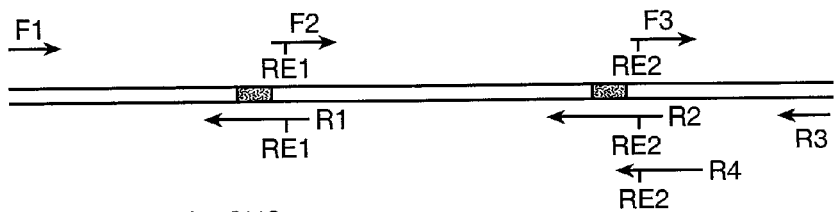

STEP 1: SET UP 3 PCR REACTIONS:

TUBE 1: 

TUBE 2: 

TUBE 3: 

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 1.

STEP 7: AMPLIFY PRODUCT FROM STEP 6 WITH F1 + R3.

FIG._7

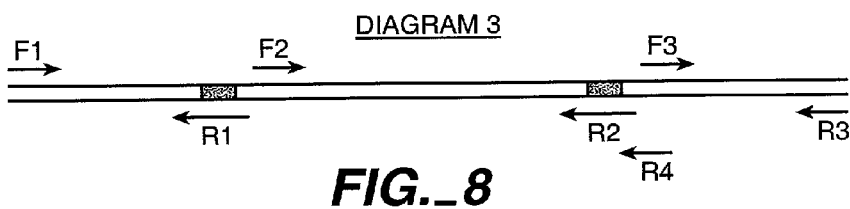

FIG._8

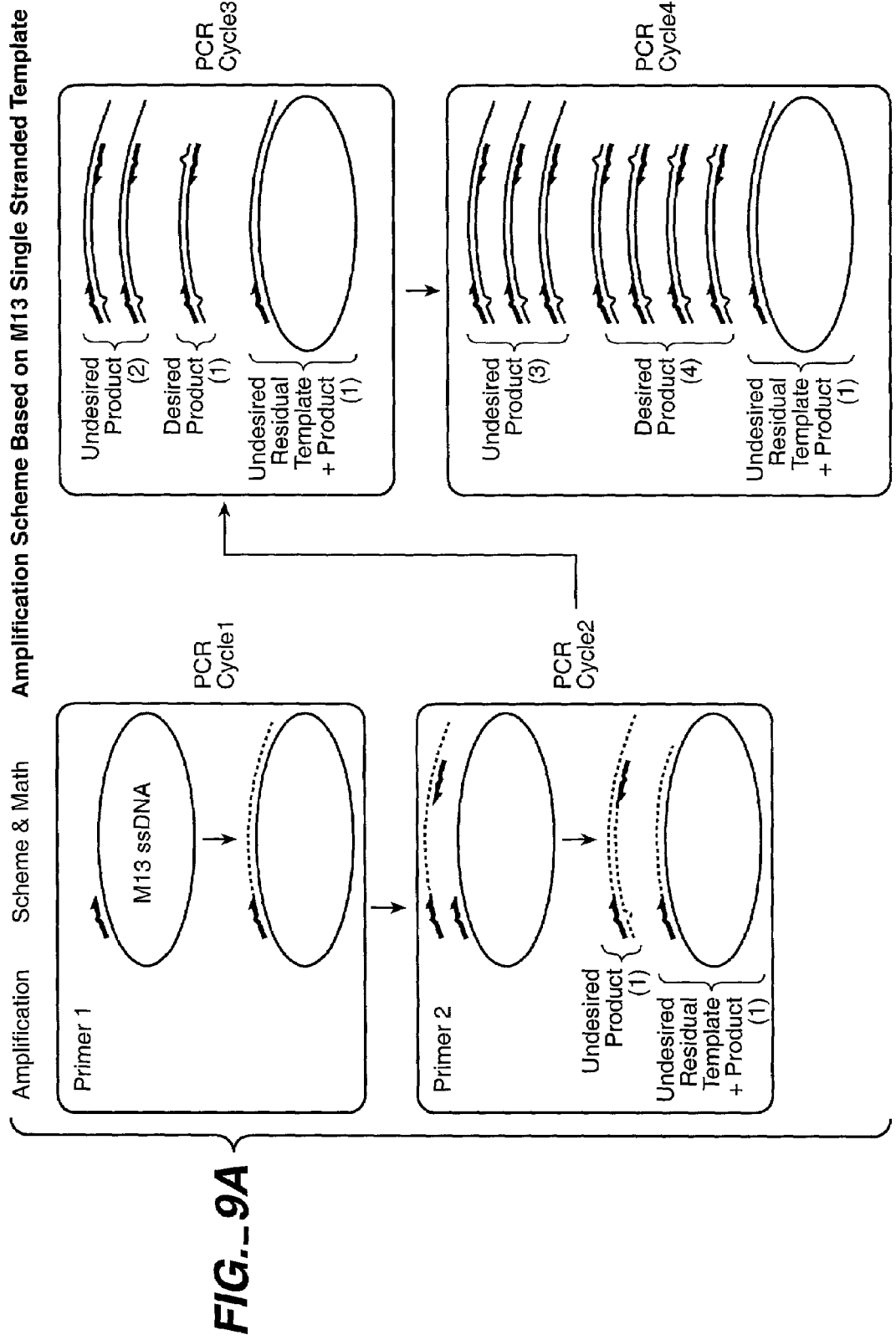
FIG._9A

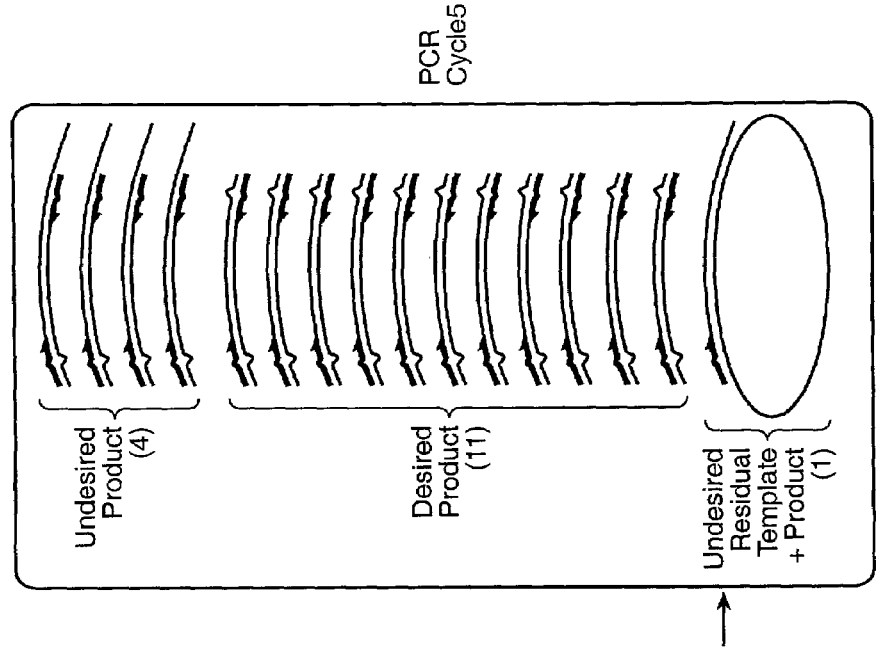
FIG._9B

PROTEIN DESIGN AUTOMATION FOR PROTEIN LIBRARIES

This application is a continuation of application Ser. No. 09/782,004, filed on Feb. 12, 2001, which claims the benefit of the filing date of Ser. Nos. 60/181,630, filed on Feb. 10, 2000; 60/186,904, filed on Mar. 3, 2000; and, 60/197,851, filed on Apr. 14, 2000, and is a continuation of Ser. No. 09/419,351, filed on Oct. 15, 1999, now U.S. Pat. No. 6,403,312, issued Jun. 11, 2002, which claims the benefit of the filing date of Ser. Nos. 60/158,700, filed Oct. 8, 1999 and 60/104,612, filed Oct. 16, 1998.

FIELD OF THE INVENTION

The invention relates to the use of a variety of computation methods, including protein design automation (PDA), to generate computationally prescreened secondary libraries of proteins, and to methods of making and methods and compositions utilizing the libraries.

BACKGROUND OF THE INVENTION

Directed molecular evolution can be used to create proteins and enzymes with novel functions and properties. Starting with a known natural protein, several rounds of mutagenesis, functional screening, and propagation of successful sequences are performed. The advantage of this process is that it can be used to rapidly evolve any protein without knowledge of its structure. Several different mutagenesis strategies exist, including point mutagenesis by error-prone PCR, cassette mutagenesis, and DNA shuffling. These techniques have had many successes; however, they are all handicapped by their inability to produce more than a tiny fraction of the potential changes. For example, there are $20^{500}$ possible amino acid changes for an average protein approximately 500 amino acids long. Clearly, the mutagenesis and functional screening of so many mutants is impossible; directed evolution provides a very sparse sampling of the possible sequences and hence examines only a small portion of possible improved proteins, typically point mutants or recombinations of existing sequences. By sampling randomly from the vast number of possible sequences, directed evolution is unbiased and broadly applicable, but inherently inefficient because it ignores all structural and biophysical knowledge of proteins.

In contrast, computational methods can be used to screen enormous sequence libraries (up to $10^{80}$ in a single calculation) overcoming the key limitation of experimental library screening methods such as directed molecular evolution. There are a wide variety of methods known for generating and evaluating sequences. These include, but are not limited to, sequence profiling (Bowie and Eisenberg, Science 253(5016): 164-70, (1991)), rotamer library selections (Dahiyat and Mayo, Protein Sci 5(5): 895-903 (1996); Dahiyat and Mayo, Science 278(5335): 82-7 (1997); Desjarlais and Handel, Pro Science 4: 2006-2018 (1995); Harbury et al, PNAS USA 92(18): 8408-8412 (1995); Kono et al., Proteins: Structure, Function and Genetics 19: 244-255 (1994); Hellinga and Richards, PNAS USA91 5803-5807 (1994)); and residue pair potentials (Jones, Protein Science 3: 567-574, (1994)).

In particular, U.S. Ser. Nos. 60/061,097, 60/043,464, 60/054,678, 09/127,926, now U.S. Pat. No. 6,269,312 and PCT US98/07254 describe a method termed "Protein Design Automation", or PDA, that utilizes a number of scoring functions to evaluate sequence stability.

It is an object of the present invention to provide computational methods for prescreening sequence libraries to generate and select secondary libraries, which can then be made and evaluated experimentally.

SUMMARY OF THE INVENTION

In accordance with the objects outlined above, the present invention provides methods for generating a secondary library of scaffold protein variants comprising providing a primary library comprising a rank-ordered list of scaffold protein primary variant sequences. A list of primary variant positions in the primary library is then generated, and a plurality of the primary variant positions is then combined to generate a secondary library of secondary sequences.

In an additional aspect, the invention provides methods for generating a secondary library of scaffold protein variants comprising providing a primary library comprising a rank-ordered list of scaffold protein primary variant sequences, and generating a probability distribution of amino acid residues in a plurality of variant positions. The plurality of the amino acid residues is combined to generate a secondary library of secondary sequences. These sequences may then be optionally synthesized and tested, in a variety of ways, including multiplexing PCR with pooled oligonucleotides, error prone PCR, gene shuffling, etc.

In a further aspect, the invention provides compositions comprising a plurality of secondary variant proteins or nucleic acids encoding the proteins, wherein the plurality comprises all or a subset of the secondary library. The invention further provides cells comprising the library, particularly mammalian cells.

In an additional aspect, the invention provides methods for generating a secondary library of scaffold protein variants comprising providing a first library rank-ordered list of scaffold protein primary variants;

generating a probability distribution of amino acid residues in a plurality of variant positions; and synthesizing a plurality of scaffold protein secondary variants comprising a plurality of the amino acid residues to form a secondary library. At least one of the secondary variants is different from the primary variants.

BRIEF DESCRIPTION OF THE DRAWINGS

FIG. 1 depicts the synthesis of a full-length gene and all possible mutations by PCR. Overlapping oligonucleotides corresponding to the full-length gene (black bar, Step 1) are synthesized, heated and annealed. Addition of Pfu DNA polymerase to the annealed oligonucleotides results in the 5'→3' synthesis of DNA (Step 2) to produce longer DNA fragments (Step 3). Repeated cycles of heating, annealing (Step 4) results in the production of longer DNA, including some full-length molecules. These can be selected by a second round of PCR using primers (arrowed) corresponding to the end of the full-length gene (Step 5).

FIG. 2 depicts the reduction of the dimensionality of sequence space by PDA screening. From left to right, 1: without PDA; 2: without PDA not counting Cysteine, Proline, Glycine; 3: with PDA using the 1% criterion, modeling free enzyme; 4: with PDA using the 1% criterion, modeling enzyme-substrate complex; 5: with PDA using the 5% criterion modeling free enzyme; 6: with PDA using the 5% criterion modeling enzyme-substrate complex.

FIG. 3 depicts the active site of *B. circulans* xylanase. Those positions included in the PDA design are shown by their side chain representation. In red are wild type residues (their conformation was allowed to change, but not their amino acid identity). In green are positions whose conformation and identity were allowed to change (to any amino acid except proline, cysteine and glycine).

FIG. 4 depicts cefotaxime resistance of *E. coli* expressing wild type (WT) and PDA Screened β-lactamase; results shown for increasing concentrations of cefotaxime.

FIG. 5 depicts a preferred scheme for synthesizing a library of the invention. The wild-type gene, or any starting gene, such as the gene for the global minima gene, can be used. Oligonucleotides comprising different amino acids at the different variant positions can be used during PCR using standard primers. This generally requires fewer oligonucleotides and can result in fewer errors.

FIG. 6 depicts and overlapping extension method. At the top of FIG. 6 is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. In this example, three separate PCR reactions are done for step 1. The first reaction contains the template plus oligos F1 and R1. The second reaction contains template plus F2 and R2, and the third contains the template and F3 and R3. The reaction products are shown. In Step 2, the products from Step 1 tube 1 and Step 1 tube 2 are taken. After purification away from the primers, these are added to a fresh PCR reaction together with F1 and R4. During the Denaturation phase of the PCR, the overlapping regions anneal and the second strand is synthesized. The product is then amplified by the outside primers. In Step 3, the purified product from Step 2 is used in a third PCR reaction, together with the product of Step 1, tube 3 and the primers F1 and R3. The final product corresponds to the full length gene and contains the required mutations.

FIG. 7 depicts a ligation of PCR reaction products to synthesize the libraries of the invention. In this technique, the primers also contain an endonuclease restriction site (RE), either blunt, 5' overhanging or 3' overhanging. We set up three separate PCR reactions for Step 1. The first reaction contains the template plus oligos F1 and R1. The second reaction contains template plus F2 and R2, and the third contains the template and F3 and R3. The reaction products are shown. In Step 2, the products of step 1 are purified and then digested with the appropriate restriction endonuclease. The digestion products from Step 2, tube 1 and Step 2, tube 2 and ligate them together with DNA ligase (step 3). The products are then amplified in Step 4 using primer F1 and R4. The whole process is then repeated by digesting the amplified products, ligating them to the digested products of Step 2, tube 3, and then amplifying the final product by primers F1 and R3. It would also be possible to ligate all three PCR products from Step 1 together in one reaction, providing the two restriction sites (RE1 and RE2) were different.

FIG. 8 depicts blunt end ligation of PCR products. In this technique, the primers such as F1 and R1 do not overlap, but they abut. Again three separate PCR reactions are performed. The products from tube 1 and tube 2 are ligated, and then amplified with outside primers F1 and R4. This product is then ligated with the product from Step 1, tube 3. The final products are then amplified with primers F1 and R3.

FIG. 9 depicts M13 single stranded template production of mutated-PCR products. Primer1 and Primer2 (each representing a pool of primers corresponding to desired mutations) are mixed with the M13 template containing the wildtype gene or any starting gene. PCR produces the desired product (11) containing the combinations of the desired mutations incorporated in Primer1 and Primer2. This scheme can be used to produce a gene with mutations, or fragments of a gene with mutations that are then linked together via ligation or PCR for example.

DETAILED DESCRIPTION OF THE INVENTION

The present invention is directed to methods of using computational screening of protein sequence libraries (that can comprise up to $10^{80}$ or more members) to select smaller libraries of protein sequences (that can comprise up to $10^{13}$ members), that can then be used in a number of ways. For example, the proteins can be actually synthesized and experimentally tested in the desired assay, for improved function and properties. Similarly, the library can be additionally computationally manipulated to create a new library which then itself can be experimentally tested.

The invention has two broad uses; first, the invention can be used to prescreen libraries based on known scaffold proteins. That is, computational screening for stability (or other properties) may be done on either the entire protein or some subset of residues, as desired and described below. By using computational methods to generate a threshold or cutoff to eliminate disfavored sequences, the percentage of useful variants in a given variant set size can increase, and the required experimental outlay is decreased.

In addition, the present invention finds use in the screening of random peptide libraries. As is known, signaling pathways in cells often begin with an effector stimulus that leads to a phenotypically describable change in cellular physiology. Despite the key role intracellular signaling pathways play in disease pathogenesis, in most cases, little is understood about a signaling pathway other than the initial stimulus and the ultimate cellular response.

Historically, signal transduction has been analyzed by biochemistry or genetics. The biochemical approach dissects a pathway in a "stepping-stone" fashion: find a molecule that acts at, or is involved in, one end of the pathway, isolate assayable quantities and then try to determine the next molecule in the pathway, either upstream or downstream of the isolated one. The genetic approach is classically a "shot in the dark": induce or derive mutants in a signaling pathway and map the locus by genetic crosses or complement the mutation with a cDNA library. Limitations of biochemical approaches include a reliance on a significant amount of pre-existing knowledge about the constituents under study and the need to carry such studies out in vitro, post-mortem. Limitations of purely genetic approaches include the need to first derive and then characterize the pathway before proceeding with identifying and cloning the gene.

Screening molecular libraries of chemical compounds for drugs that regulate signal systems has led to important discoveries of great clinical significance. Cyclosporin A (CsA) and FK506, for examples, were selected in standard pharmaceutical screens for inhibition of T-cell activation. It is noteworthy that while these two drugs bind completely different cellular proteins—cyclophilin and FK506 binding protein (FKBP), respectively, the effect of either drug is virtually the same—profound and specific suppression of T-cell activation, phenotypically observable in T cells as inhibition of mRNA production dependent on transcription factors such as NF-AT and NF-κB. Libraries of small peptides have also been successfully screened in vitro in assays for bioactivity The literature is replete with examples of small peptides capable of modulating a wide variety of signaling pathways. For example, a peptide derived from the HIV-1 envelope protein has been shown to block the action of cellular calmodulin.

Accordingly, generation of random or semi-random sequence libraries of proteins and peptides allows for the selection of proteins (including peptides, oligopeptides and polypeptides) with useful properties. The sequences in these experimental libraries can be randomized at specific sites only, or throughout the sequence. The number of sequences that can be searched in these libraries grows exponentially with the number of positions that are randomized. Generally, only up to $10^{12}$-$10^{15}$ sequences can be contained in a library because of the physical constraints of laboratories (the size of the instruments, the cost of producing large numbers of biopolymers, etc.). Other practical considerations can often limit the size of the libraries to $10^6$ or fewer. These limits are reached for only 10 amino acid positions. Therefore, only a sparse sampling of sequences is possible in the search for improved proteins or peptides in experimental sequence libraries, lowering the chance of success and almost certainly missing desirable candidates. Because of the randomness of the changes in these sequences, most of the candidates in the library are not suitable, resulting in a waste of most of the effort in producing the library.

However, using the automated protein design techniques outlined below, virtual libraries of protein sequences can be generated that are vastly larger than experimental libraries. Up to $10^{80}$ candidate sequences can be screened computationally and those that meet design criteria which favor stable and functional proteins can be readily selected. An experimental library consisting of the favorable candidates found in the virtual library screening can then be generated, resulting in a much more efficient use of the experimental library and overcoming the limitations of random protein libraries.

Two principle benefits come from the virtual library screening: (1) the automated protein design generates a list of sequence candidates that are favored to meet design criteria; it also shows which positions in the sequence are readily changed and which positions are unlikely to change without disrupting protein stability and function. An experimental random library can be generated that is only randomized at the readily changeable, non-disruptive sequence positions. (2) The diversity of amino acids at these positions can be limited to those that the automated design shows are compatible with these positions. Thus, by limiting the number of randomized positions and the number of possibilities at these positions, the number of wasted sequences produced in the experimental library is reduced, thereby increasing the probability of success in finding sequences with useful properties.

In addition, by computationally screening very large libraries of mutants, greater diversity of protein sequences can be screened (i.e. a larger sampling of sequence space), leading to greater improvements in protein function. Further, fewer mutants need to be tested experimentally to screen a given library size, reducing the cost and difficulty of protein engineering. By using computational methods to pre-screen a protein library, the computational features of speed and efficiency are combined with the ability of experimental library screening to create new activities in proteins for which appropriate computational models and structure-function relationships are unclear.

Similarly, novel methods to create secondary libraries derived from very large computational mutant libraries allow the rapid testing of large numbers of computationally designed sequences.

In addition, as is more fully outlined below, the libraries may be biased in any number of ways, allowing the generation of secondary libraries that vary in their focus; for example, domains, subsets of residues, active or binding sites, surface residues, etc., may all be varied or kept constant as desired.

In general, as more fully outlined below, the invention can take on a wide variety of configurations. In general, primary libraries, e.g. libraries of all or a subset of possible proteins are generated computationally. This can be done in a wide variety of ways, including sequence alignments of related proteins, structural alignments, structural prediction models, databases, or (preferably) protein design automation computational analysis. Similarly, primary libraries can be generated via sequence screening using a set of scaffold structures that are created by perturbing the starting structure (using any number of techniques such as molecular dynamics, Monte Carlo analysis) to make changes to the protein (including backbone and sidechain torsion angle changes). Optimal sequences can be selected for each starting structures (or, some set of the top sequences) to make primary libraries.

Some of these techniques result in the list of sequences in the primary library being "scored", or "ranked" on the basis of some particular criteria. In some embodiments, lists of sequences that are generated without ranking can then be ranked using techniques as outlined below.

In a preferred embodiment, some subset of the primary library is then experimentally generated to form a secondary library. Alternatively, some or all of the primary library members are recombined to form a secondary library, e.g. with new members. Again, this may be done either computationally or experimentally or both.

Alternatively, once the primary library is generated, it can be manipulated in a variety of ways. In one embodiment, a different type of computational analysis can be done; for example, a new type of ranking may be done. Alternatively, and the primary library can be recombined, e.g. residues at different positions mixed to form a new, secondary library. Again, this can be done either computationally or experimentally, or both.

Accordingly, the present invention provides methods for generating secondary libraries of scaffold protein variants. By "protein" herein is meant at least two amino acids linked together by a peptide bond. As used herein, protein includes proteins, oligopeptides and peptides. The peptidyl group may comprise naturally occurring amino acids and peptide bonds, or synthetic peptidomimetic structures, i.e. "analogs", such as peptoids (see Simon et al., *PNAS USA* 89(20):9367 (1992)). The amino acids may either be naturally occurring or non-naturally occurring; as will be appreciated by those in the art, any structure for which a set of rotamers is known or can be generated can be used as an amino acid The side chains may be in either the (R) or the (S) configuration. In a preferred embodiment, the amino acids are in the (S) or L-configuration.

The scaffold protein may be any protein for which a three dimensional structure is known or can be generated; that is, for which there are three dimensional coordinates for each atom of the protein.

Generally this can be determined using X-ray crystallographic techniques, NMR techniques, de novo modelling, homology modelling, etc. In general, if X-ray structures are used, structures at 2Å resolution or better are preferred, but not required.

The scaffold proteins may be from any organism, including prokaryotes and eukaryotes, with enzymes from bacteria, fungi, extremeophiles such as the archebacteria, insects, fish, animals (particularly mammals and particularly human) and birds all possible.

Thus, by "scaffold protein" herein is meant a protein for which a secondary library of variants is desired. As will be appreciated by those in the art, any number of scaffold proteins find use in the present invention. Specifically included within the definition of "protein" are fragments and domains of known proteins, including functional domains such as enzymatic domains, binding domains, etc., and smaller fragments, such as turns, loops, etc. That is, portions of proteins may be used as well. In addition, "protein" as used herein includes proteins, oligopeptides and peptides. In addition, protein variants, i.e. non-naturally occurring protein analog structures, may be used.

Suitable proteins include, but are not limited to, industrial and pharmaceutical proteins, including ligands, cell surface receptors, antigens, antibodies, cytokines, hormones, transcription factors, signaling modules, cytoskeletal proteins and enzymes. Suitable classes of enzymes include, but are not limited to, hydrolases such as proteases, carbohydrases, lipases; isomerases such as racemases, epimerases, tautomerases, or mutases; transferases, kinases, oxidoreductases, and phophatases. Suitable enzymes are listed in the Swiss-Prot enzyme database. Suitable protein backbones include, but are not limited to, all of those found in the protein data base compiled and serviced by the Research Collaboratory for Structural Bioinformatics (RCSB, formerly the Brookhaven National Lab).

Specifically, preferred scaffold proteins include, but are not limited to, those with known structures (including variants) including cytokines (IL-1ra(+receptor complex), IL-1 (receptor alone), IL-1a, IL-1b (including variants and or receptor complex), IL-2, IL-3, IL4, IL-5, IL-6, IL-8, IL-10, IFN-β, INF-γ, IFN-α-2a; IFN-α-2B, TNF-α; CD40 ligand (chk), Human Obesity Protein Leptin, Granulocyte Colony-Stimulating Factor, Bone Morphogenetic Protein-7, Ciliary Neurotrophic Factor, Granulocyte-Macrophage Colony-Stimulating Factor, Monocyte Chemoattractant Protein 1, Macrophage Migration Inhibitory Factor, Human Glycosylation-Inhibiting Factor, Human Rantes, Human Macrophage inflammatory Protein 1 Beta, human growth hormone, Leukemia Inhibitory Factor, Human Melanoma Growth Stimulatory Activity, neutrophil activating peptide-2, Cc-Chemokine Mcp-3, Platelet Factor M2, Neutrophil Activating Peptide 2, Eotaxin, Stromal Cell-Derived Factor-1, Insulin, Insulin-like Growth Factor I, Insulin-like Growth Factor II, Transforming Growth Factor B1, Transforming Growth Factor B2, Transforming Growth Factor B3, Transforming Growth Factor A, Vascular Endothelial growth factor (VEGF), acidic Fibroblast growth factor, basic Fibroblast growth factor, Endothelial growth factor, Nerve growth factor, Brain Derived Neurotrophic Factor, Ciliary Neurotrophic Factor, Platelet Derived Growth Factor, Human Hepatocyte Growth Factor, Glial Cell-Derived Neurotrophic Factor, (as well as the 55 cytokines in PDB Jan. 12, 1999)); Erythropoietin; other extracellular signalling moeities, including, but not limited to, hedgehog Sonic, hedgehog Desert, hedgehog Indian, hCG; coaguation factors including, but not limited to, TPA and Factor VIIa; transcription factors, including but not limited to, p53, p53 tetramerization domain, Zn fingers (of which more than 12 have structures), homeodomains (of which 8 have structures), leucine zippers (of which 4 have structures); antibodies, including, but not limited to, cFv; viral proteins, including, but not limited to, hemagglutinin trimerization domain and hiv Gp41 ectodomain (fusion domain); intracellular signalling modules, including, but not limited to, SH2 domains (of which 8 structures are known), SH3 domains (of which 11 have structures), and Pleckstin Homology Domains; receptors, including, but not limited to, the extracellular Region Of Human Tissue Factor Cytokine-Binding Region Of Gp130, G-CSF receptor, erythropoietin receptor, Fibroblast Growth Factor receptor, TNF receptor, IL-1 receptor, IL-1 receptor/IL-1ra complex, IL-4 receptor, INF-γreceptor alpha chain, MHC Class I, MHC Class II, T Cell Receptor, Insulin receptor, insulin receptor tyrosine kinase and human growth hormone receptor.

Once a scaffold protein is chosen, a primary library is generated using computational processing. Generally speaking, in some embodiments, the goal of the computational processing is to determine a set of optimized protein sequences. By "optimized protein sequence" herein is meant a sequence that best fits the mathematical equations of the computational process. As will be appreciated by those in the art, a global optimized sequence is the one sequence that best fits the equations (for example, when PDA is used, the global optimzed sequence is the sequence that best fits Equation 1, below); i.e. the sequence that has the lowest energy of any possible sequence. However, there are any number of sequences that are not the global minimum but that have low energies.

Thus, a "primary library" as used herein is a collection of optimized sequences, generally, but not always, in the form of a rank-ordered list. In theory, all possible sequences of a protein may be ranked; however, currently $10^{13}$ sequences is a practical limit. Thus, in general, some subset of all possible sequences is used as the primary library; generally, the top $10^3$ to $10^3$ sequences are chosen as the primary library. The cutoff for inclusion in the rank ordered list of the primary library can be done in a variety of ways. For example, the cutoff may be just an arbitrary exclusion point: the top $10^5$ sequences may comprise the primary library. Alternatively, all sequences scoring within a certain limit of the global optimum can be used; for example, all sequences with 10 kcal/mol of the global optimum could be used as the primary library. This method has the advantage of using a direct measure of fidelity to a three dimensional structure to determine inclusion. This approach can be used to insure that library mutations are not limited to positions that have the lowest energy gap between different mutations. Alternatively, the cutoff may be enforced when a predetermined number of mutations per position is reached. As a rank ordered sequence list is lengthened and the library is enlarged, more mutations per position are defined. Alternatively, the total number of sequences defined by the recombination of all mutations can be used as a cutoff criterion for the primary sequence library. Preferred values for the total number of sequences range from 100 to $10^{20}$, particularly preferred values range from 1000 to $10^{13}$, especially preferred values range from 1000 to $10^7$ Alternatively, the first occurrence in the list of predefined undesirable residues can be used as a cutoff criterion. For example, the first hydrophilic residue occurring in a core position would limit the list. It should also be noted that while these methods are described in conjunction with limiting the size of the primary library, these same techniques may be used to formulate the cutoff for inclusion in the secondary library as well.

Thus, the present invention provides methods to generate a primary library optionally comprising a rank ordered list of sequences, generally in terms of theoretical quantitative stability, as is more fully described below. Generating a primary library to optimize the stability of a conformation can be used to stabilize the active site transition state conformation of an enzyme, which will improve its activity. Similarly, stabilizing a ligand-receptor complex or enzyme-substrate complex will improve the binding affinity.

The primary libraries can be generated in a variety of ways. In essence, any methods that can result in either the relative ranking of the possible sequences of a protein based on measurable stability parameters, or a list of suitable sequences can be used. As will be appreciated by those in the art, any of the methods described herein or known in the art may be used alone, or in combination with other methods.

Generally, there are a variety of computational methods that can be used to generate a primary library. In a preferred embodiment, sequence based methods are used. Alternatively, structure based methods, such as PDA, described in detail below, are used.

In a preferred embodiment, the scaffold protein is an enzyme and highly accurate electrostatic models can be used for enzyme active site residue scoring to improve enzyme active site libraries (see Warshel, *computer Modeling of Chemical Reactions in Enzymes and Solutions*, Wiley & Sons, New York, (1991), hereby expressly incorporated by reference) These accurate models can assess the relative energies of sequences with high precision, but are computationally intensive.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534-552 (1985), expressly incorporated by reference) during computational screening.

In a preferred embodiment, sequence profile scores (Bowie et al., Science 253(5016):164-70 (1991), incorporated by reference) and/or potentials of mean force (Hendlich et al., J. Mol. Biol. 216(1):167-180 (1990), also incorporated by reference) can also be calculated to score sequences. These assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1-8 (1998), hereby expressly incorporated by reference). Similarly, scoring functions can be used to screen for sequences that would create disulfide bonds in the protein. These potentials attempt to specifically modify a protein structure to introduce a new structural motif.

In a preferred embodiment, sequence and/or structural alignment programs can be used to generate primary libraries. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

The source of the sequences can vary widely, and include taking sequences from one or more of the known databases, including, but not limited to, SCOP (Hubbard, et al., Nucleic Acids Res 27(1):254-256. (1999)); PFAM (Bateman, et al., Nucleic Acids Res 27(1):260-262. (1999)); VAST (Gibrat, Ct al., Curr Opin Struct Bid 6(3):377-385. (1996)); CATH (Orengo, et al., Structure 5(8):1093-1108. (1997)); PhD Predictor (Rost B, Sander C, Schneider R, PHD—an automatic mail server for protein secondary structure prediction. Comput Appl Biosci. 1994 Feb; 10(1):53-60); Prosite (Hofmann, et al., Nucleic Acids Res 27(1):215-219, (1999)); PIR (Wu CH, Yeh LS, Huang H, Arminski L, Castro-Alvcar J, Chen Y, Hu Z, Kourtesis P, Ledley R S, Suzek B E. Vinayaka C R, Zhang J, Barker W C, The Protein Information Resource, Nucleic Acids Res. 2003 Jan 1; 31(1):345-7.); GenBank (nebi.nlm.nih.gov); PDB (H. M. Berman, T. Battistuz, T. N. Bhat, W. F. Bluhm, P. E. Bourne, K. Burkhardt, Z. Feng, G. L. (Gilliland, L. Iype, S. Jain, P. Fagan, J. Marvin, D. Padilla, V. Ravichandran, B. Schneider, N. Thanki, H. Weissig, J. D. Westbrook and C. Zardecki, The Protein Data Bank, Acta Cryst. (2002). D58, 899-907) and BIND (Bader, et al., Nucleic Acids Res 29(1):242-245, (2001)).

In addition, sequences from these databases can be subjected to continguous analysis or gene prediction; see Wheeler, et al., Nucleic Acids Res 28(1):10-14. (2000) and Burge and Karlin, J Mol Biol 268(1):78-94. (1997).

As is known in the art, there are a number of sequence alignment methodologies that can be used. For example, sequence homology based alignment methods can be used to create sequence alignments of proteins related to the target structure (Altschul et al., J. Mol. Biol. 215(3):403 (1990), incorporated by reference). These sequence alignments are then examined to determine the observed sequence variations. These sequence variations are tabulated to define a primary library. In addition, as is further outlined below, these methods can also be used to generate secondary libraries.

Sequence based alignments can be used in a variety of ways. For example, a number of related proteins can be aligned, as is known in the art, and the "variable" and "conserved" residues defined; that is, the residues that vary or remain identical between the family members can be defined. These results can be used to generate a probability table, as outlined below. Similarly, these sequence variations can be tabulated and a secondary library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused primary library but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) can be randomized, either using all or a subset of amino acids. Similarly, outlier residues, either positional outliers or side chain outliers, may be eliminated.

Similarly, structural alignment of structurally related proteins can be done to generate sequence alignments. There are a wide variety of such structural alignment programs known, See for example VAST from the NCBI (Gibrat, et al., Curr Opin Struct Biol 6(3):377-385. (1996)); SSAP (Orengo and Taylor, Methods Enzymol 266(617-635 (1996)) SARF2 (Alexandrov, Protein Eng 9(9):727-732. (1996) CE (Shindyalov and Bourne, Protein Eng 11(9):739-747. (1998)); (Orengo et al., Structure 5(8):1093-108 (1997); Dali (Holm et al., Nucleic Acid Res. 26(1):316-9 (1998), all of which are incorporated by reference). These structurally-generated sequence alignments can then be examined to determine the observed sequence variations.

Primary libraries can be generated by predicting secondary structure from sequence, and then selecting sequences that arc compatible with the predicted secondary structure. There are a number of secondary structure prediction methods, including, but not limited to, threading (Bryant and Altschul, Curr Opin Struct Biol 5(2):236-244. (1995)), Profile 3D (Bowie, et al., Methods Enzymol 266(598-616 (1996); MONSSTER (Skolnick, et al., J Mol Biol 265(2): 217-241. (1997); Rosetta (Simons, et al., Proteins 37(S3): 171-176 (1999); PSI-BLAST (Altschul and Koonin, Trends Biochem Sci 23(11 ):444-447(1998)); Impala (Schaffer, et al., Bioinformatics 15(12):1000-1011. (1999)); HMMER (McClure, at al., Proc Int Conf Intell Syst Mol Biol 4(155-164 (1996)); Clustal W Higgins D., Thompson J., Gibson T. Thompson J. D., Higgins D. G., Gibson T. J. (1994). CLUSTAL W: improving the sensitivity of progressive multiple sequence alignment through sequence weighting, position-specific gap penalties and weight matrix choice. Nucleic Acids Res. 22:4673-4680; BLAST (Altschul, et al., J Mol Biol 215(3):403-410. (1990)), helix-coil transition theory (Munoz and Serrano, Biopolymers 41:495, 1997), neural networks, local structure alignment and others (e.g., see in Selbig et al., Bioinformatics 15:1039, 1999).

Similarly, as outlined above, other computational methods are known, including, but not limited to, sequence profiling (Bowie and Eisenberg, Science 253(5016): 164-70, (1991)), rotamer library selections (Dahiyat and Mayo, Protein Sci 5(5): 895-903 (1996); Dahiyat and Mayo, Science 278(5335): 82-7 (1997); Desjarlais and Handel, Protein Science 4: 2006-2018 (1995); Harbury et al, PNAS USA 92(18): 8408-8412 (1995); Kono et al., Proteins: Structure, Function and Genetics 19: 244-255 (1994); Hellinga and Richards, PNAS USA 91: 5803-5807 (1994)); and residue pair potentials (Jones, Protein Science 3: 567-574, (1994); PROSA (Heindlich et al., J. Mol. Biol. 216:167-180 (1990); THREADER (Jones et al., Nature 358:8689(1992), and other inverse folding methods such as those described by Simons et al. (Proteins, 34:535-543, 1999), Levitt and Gerstein (PNAS USA, 95:5913-5920,1998), Godzik et al., PNAS, V89, PP 12098-102; Godzik and Skolnick (PNAS USA, 89:12098-102, 1992), Godzik et al. (J. Mol. Biol. 227:227-38, 1992) and two profile methods (Gribskov et al. PNAS 84:4355-4358 (1987) and Fischer and Eisenberg, Protein Sci. 5:947-955 (1996), Rice and Eisenberg J. Mol. Biol. 267:1026-1038(1997)), all of which are expressly incorporated by reference. In addition, other computational methods such as those described by Koehl and Levitt (J. Mol. Biol. 293:1161-1181 (1999); J. Mol. Biol. 293:1183-1193 (1999); expressly incorporated by reference) can be used to create a protein sequence library which can optionally then be used to generate a smaller secondary library for use in experimental screening for improved properties and function.

In addition, there are computational methods based on forcefield calculations such as SCMF that can be used as well for SCMF, see Delarue et al., Pac. Symp. Biocomput. 109-21 (1997), Koehl et al., J. Mol. Biol. 239:249 (1994); Koehl et al., Nat. Struc. Biol. 2:163 (1995); Koehl et al., Curr. Opin. Strut. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53-70 (1995); all of which are expressly incorporated by reference. Other forcefield calculations that can be used to optimize the conformation of a sequence within a computational method, or to generate de novo optimized sequences as outlined herein include, but are not limited to, OPLS-AA (Jorgensen, et al., J. Am. Chem. Soc. (1996), v 118, pp 11225-11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (11993), v 2, pp1697-1714; Liwo, et al., Protein Science (1993), v 2, pp1715-1731; Liwo, et al., J. Comp. Chem. (1997), v 18, pp849-873; Liwo, et al., J. Comp. Chem. (1997), v 18, pp874-884; Liwo, et al., J. Comp. Chem. (1998), v 19, pp259-276; Forcefield for Protein Structure Prediction (Liwo, et al., Proc. Natl. Acad. Sci. USA (1999), v 96, pp5482-5485); ECEPP/3 (Liwo et al., J Protein Chem 1994 May; 13(4):375-80); AMBER 1.1 force field (Weiner, et al., J. Am. Chem. Soc. v106, pp765-784); AMBER 3.0 force field (U. C. Singh et al., Proc. Natl. Acad. Sci. USA. 82:755-759); CHARMM and CHARMM22 (Brooks, et al., J. Comp. Chem. v4, pp 187-217); cvff3.0 (Dauber-Osguthorpe, et al., (1988) Proteins: Structure, Function and Genetics, v4,pp31-47); cff91 (Maple, et al., J. Comp. Chem. v15, 162-182); also, the DISCOVER (cvff and cff91) and AMBER forcefields are used in the INSIGHT molecular modeling package (Biosym/ MSI, San Diego Calif.) and HARMM is used in the QUANTA molecular modeling package (Biosym/MSI, San Diego Calif.), all of which are expressly incorporated by reference. In fact, as is outlined below, these forcefield methods may be used to generate the secondary library directly; that is, no primary library is generated; rather, these methods can be used to generate a probability table from which the secondary library is directly generated, for example by using these forcefields during an SCMF calculation.

In a preferred embodiment, a three dimensional database is created by modifying a known protein structure to incorporate particular amino acid residues required for a characteristic property or function, as is described in WO 00/23474, expressly incorporated herein by reference. This database can be searched to identify new proteins having structural similarity with the known protein.

In a preferred embodiment, a sequence prediction algorithm (SPA) is used to design proteins that are compatible with a known protein backbone structure as is described in Raha, K., et al. (2000) *Protein Sci.,* 9:1106-1119, expressly incorporated herein by reference.

In a preferred embodiment, the computational method used to generate the primary library is Protein Design Automation (PDA), as is described in U.S. Ser. Nos. 60/061, 097, 60/043,464, 60/054,678, 09/127,926 now U.S. Pat. No. 6,269,312, and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Similarly, for all the sampling techniques, the acceptance criteria of whether a sampling jump is accepted can be altered.

As outlined in U.S. Ser. No. 09/127,926, now U.S. Pat. No. 6,269,312, the protein backbone (comprising (for a naturally occurring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization (Mayo et al., *J. Phys. Chem.* 94:8897 (1990)) of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occuring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which form the active site of an enzyme, the substrate binding site of an enzyme, the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

In a preferred embodiment, each variable position is classified as either a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modelling. Alternatively, a preferred embodiment utilizes an assessment of the orientation of the $C\alpha$-$C\beta$ vectors relative to a solvent accessible surface computed using only the template $C\alpha$ atoms, as outlined in U.S. Ser. Nos. 60/061,097, 60/043,464, 60/054,678, 09/127,926 now U.S. Pat. No. 6,269,312, and PCT US98/07254. Alternatively, a surface area calculation can be done.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the $\alpha$ scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occuring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an $\alpha$-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a $\phi$ angle (that is, the dihedral angle defined by 1) the carbonyl carbon of the preceding amino acid; 2) the nitrogen atom of the current residue; 3) the $\alpha$-carbon of the current residue; and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127,926 now U.S. Pat. No. 6,269,312, and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic salvation scoring function, a secondary structure propensity scoring function and an electrostatic scoring function. As is further described below, at least one scoring function is used to score each position, although the scoring functions may differ depending on the position classification or other considerations, like favorable interaction with an $\alpha$-helix dipole. As outlined below, the total energy which is used in the calculations is the sum of the energy of each scoring function used at a particular position, as is generally shown in Equation 1:

$$E_{total}=nE_{vdw}+nE_{as}+nE_{h\text{-}bonding}+nE_{ss}+nE_{elec} \quad \text{Equation 1}$$

In Equation 1, the total energy is the sum of the energy of the van der Waals potential ($E_{vdw}$), the energy of atomic salvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926 now U.S. Pat. No. 6,269,312, and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered. The term "portion", as used herein, with regard to a protein refers to a fragment of that protein. This fragment may range in size from 10 amino acid residues to the entire amino acid sequence minus one amino acid. Accordingly, the term "portion", as used herein, with regard to a nucleic refers to a fragment of that nucleic acid. This fragment may range in size from 10 nucleotides to the entire nucleic acid sequence minus one nucleotide.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdw}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function every atom of the first rotamer is compared to every atom of every possible second rotamer, and the $E_{vdw}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

In addition, as will be appreciated by those in the art, a variety of force fields that can be used in the PCA calculations can be used, including, but not limited to, Dreiding I and Dreiding II (Mayo et al, J. Phys. Chem. 948897 (1990)), AMBER (Weiner et al., J. Amer. Chem. Soc. 106:765 (1984) and Weiner et al., J. Comp. Chem. 106:230 (1986)), MM2 (Allinger J. Chem. Soc. 99:8127 (1977), Liljefors et al., J. Com. Chem. 8:1051 (1987)); MMP2 (Sprague et al., J. Comp. Chem. 8:581 (1987)); CHARMM (Brooks et al., J. Comp. Chem. 106:187 (1983)); GROMOS; and MM3 (Allinger et al., J. Amer. Chem. Soc. 111:8551 (1989)), OPLS-AA (Jorgensen, et al., J. Am. Chem. Soc. (1996), v 118, pp 11225-11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (1993), v 2, pp1697-1714; Liwo, et al., Protein Science (1993), v 2, pp1715-1731; Liwo, et al., J. Comp. Chem. (1997), v 18, pp849-873; Liwo, et al., J. Comp. Chem. (1997), v 18, pp874-884; Liwo et al., J. Comp. Chem. (1998), v 19, pp259-276; Forcefield for Protein Structure Prediction (Liwo, et al., Proc. Natl. Acad. Sci. USA (1999), v 96, pp5482-5485); ECEPP/3 (Liwo et al., J Protein Chem 1994 May; 13(4):375-80); AMBER 1.1 force field (Weiner, et al., J. Am. Chem. Soc. v106, pp765-784); AMBER 3.0 force field (U.C. Singh et al., Proc. Natl. Acad. Sci. USA. 82:755-759); CHARMM and CHARMM22 (Brooks, et al., J. Comp. Chem. v4, pp 187-217); cvff3.0 (Dauber-Osguthorpe, et al., (1988) Proteins: Structure, Function and Genetics, v4,pp3l47); cff91 (Maple, et al., J. Comp. Chem. v15, 162-182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Ser. No. 09/127,926 now U.S. Pat. No. 6,269,312, and PCT US98/07254, preferred embodiments utilize a Dead End Elimination (DEE) step, and preferably a Monte Carlo step.

PDA, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild-type or homolog residues may be used. Similarly, the entire protein or a fragment of it may be biased; for example, the active site may be biased towards wild-type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompatibility Complex) can be used to rescore a library in order to eliminate proteins containing sequences which can potentially bind to MHC, i.e. potentially immunogenic sequences.

In a preferred embodiment, a variety of filtering techniques can be done, including, but not limited to, DEE and its related counterparts. Additional filtering techniques include, but are not limited to branch-and-bound techniques for finding optimal sequences (Gordon and Majo, Structure Fold. Des. 7:1089-98, 1999), and exhaustive enumeration of sequences. It should be noted however, that some techniques may also be done without any filtering techniques; for example, sampling techniques can be used to find good sequences, in the absence of filtering.

As will be appreciated by those in the art, once an optimized sequence or set of sequences is generated, (or again, these need not be optimized or ordered) a variety of sequence space sampling methods can be done, either in addition to the preferred Monte Carlo methods, or instead of a Monte Carlo search. That is once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Jumps where multiple residue positions are coupled (two residues always change together, or never change together), jumps where whole sets of residues change to other sequences (e.g., recombination).

Similarly, for all the sampling techniques, the acceptance criteria of whether a sampling jump is accepted can be altered, to allow broad searches at high temperature and narrow searches close to local optima at low temperatures. See Metropolis et al., J. Chem Phys v21, pp 1087, 1953, hereby expressly incorporated by reference.

In addition, it should be noted that the preferred methods of the invention result in a rank ordered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzman sampling is done. As will be appreciated by those in the art, the temperature criteria for Boltzman sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artificial Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps can occur with different crossover positions and more than one recombination at a time, and can involve recombination of two or more sequences. Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. (Science, 220:671-680, 1983). Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods can be used to further process a secondary library to generate additional secondary libraries (sometimes referred to herein as tertiary libraries).

Thus, the primary library can be generated in a variety of computational ways, including structure based methods such as PDA, or sequence based methods, or combinations as outlined herein.

Accordingly, the computational processing results in a set of sequences, that may be optimized protein sequences if some sort of ranking or scoring functions are used. These optimized protein sequences are generally, but not always, significantly different from the wild-type sequence from which the backbone was taken. That is, each optimized protein sequence preferably comprises at least about 5-10% variant amino acids from the starting or wild-type sequence, with at least about 15-20% changes being preferred and at least about 30% changes being particularly preferred.

The cutoff for the primary library is then enforced, resulting in a filtered set of primary sequences forming the primary library. By "filtered set" herein is meant the optimized protein sequences that are generated using some sort of ranking or scoring function. Although in some cases, the set may comprise an arbitrary or random selection of a subset of the primary sequences. In a preferred embodiment, the filtered set comprises a rank ordered list of sequences. As outlined above, this may be done in a variety of ways, including an arbitrary cutoff, an energy limitation, or when a certain number of residue positions have been varied. In general, the size of the primary library will vary with the size of the protein, the number of residues that are changing, the computational methods used, the cutoff applied and the discretion of the user. In general, it is preferable to have the primary library be large enough to randomly sample a reasonable sequence space to allow for robust secondary libraries. Thus, primary libraries that range from about 50 to about 1013 are preferred, with from about 1000 to about $10^7$ being particularly preferred, and from about 1000 to about 100,000 being especially preferred.

In a preferred embodiment when scoring is used, although this is not required, the primary library comprises the globally optimal sequence in its optimal conformation, i.e. the optimum rotamer at each variable position. That is, computational processing is run until the simulation program converges on a single sequence which is the global optimum. In a preferred embodiment, the primary library comprises at least two optimized protein sequences. Thus for example, the computational processing step may eliminate a number of disfavored combinations but be stopped prior to convergence, providing a library of sequences of which the global optimum is one. In addition, further computational analysis, for example using a different method, may be run on the library, to further eliminate sequences or rank them differently. Alternatively, as is more fully described in U.S. Ser. Nos. 60/061,097, 60/043,464, 601054,678, 09/127,926 now U.S. Pat. No. 6,269,312, and PCT US98/07254, the global optimum may be reached, and then further computational processing may occur, which generates additional optimized sequences in the neighborhood of the global optimum.

In addition, in some embodiments, primary library sequences that did not make the cutoff are included in the primary library. This may be desirable in some situations to evaluate the primary library generation method, to serve as controls or comparisons, or to sample additional sequence space. For example, in a preferred embodiment, the wild-type sequence is included.

It should also be noted that different ranking systems can be used. For example, a list of naturally occurring sequences can be used to calculate all possible recombinations of these sequences, with an optional rank ordering step. Alternatively, once a primary library is generated, one could rank order only those recombinations that occur at cross-over points with at least a threshold of identity over a given window. For example, 100% identity over a window of 6 amino acids, or 80% identity over a window of 10 amino acids. Alternatively, as for all the systems outlined herein, the homology could be considered at the DNA level, by computationally considering the translation fo the amino acids to their respective DNA codons. Different codon usages could be considered. A preferred embodiment considers only recombinations with corssover points that have DNA sequence identity sufficient for DNA hybridization of the differing sequences.

As is further outlined below, It should also be noted that combining different primary libraries may be done. For example, positions in a protein that show a great deal of mutational diversity in computational screening can be fixed as outlined below and a different primary library regenerated. A rank ordered list of the same length as the first would now show diversity in previously rarely changing positions. The variants from the first primary library can be combined with the variants from the second primary library to provide a combined library at lower computational cost than creating a very long rank ordered list. This approach can be particularly useful to sample sequence diversity in both low energy gap, readily changing surface positions and high energy gap, rarely changing core positions. In addition, primary libraries can be generated by combining one or more of the different calculations to form one big primary library.

Thus, the present invention provides primary libraries comprising a list of computationally derived sequences. In a preferred embodiment, these sequences are in the form of a rank ordered list. From this primary library, a secondary library is generated. As outlined herein, there are a number of different ways to generate a secondary library.

In a preferred embodiment, the primary library of the scaffold protein is used to generate a secondary library. As will be appreciated by those in the art, the secondary library can be either a subset of the primary library, or contain new library members, i.e. sequences that are not found in the primary library. That is, in general, the variant positions and/or amino acid residues in the variant positions can be recombined in any number of ways to form a new library that exploits the sequence variations found in the primary library. That is, having identified "hot spots" or important variant positions and/or residues, these positions can be recombined in novel ways to generate novel sequences to form a secondary library. Thus, in a preferred embodiment, the secondary library comprises at least one member sequence that is not found in the primary library, and preferably a plurality of such sequences.

In one embodiment, all or a portion of the primary library serves as the secondary library. That is, a cutoff is applied to the primary sequences and these sequences serve as the secondary library, without further manipulation or recombination. The library members can be made as outlined below, e.g. by direct synthesis or by constructing the nucleic acids encoding the library members, expressing them in a suitable host, optionally followed by screening.

In a preferred embodiment, the secondary library is generated by tabulating the amino acid positions that vary from a reference sequence. The reference sequence can be arbitrarily selected, or preferably is chosen either as the wild-type sequence or the global optimum sequence, with the latter being preferred That is, each amino acid position that varies in the primary library is tabulated. Of course, if the original computational analysis fixed some positions, the variable positions of the secondary library will comprise either just these original variable positions or some subset of these original variable positions. That is, assuming a protein of 100 amino acids, the original computational screen can allow all 100 positions to be varied. However, due to the cutoff in the primary library, only 25 positions may vary. Alternatively, assuming the same 100 amino acid protein, the original computational screen could have varied only 25 positions, keeping the other 75 fixed; this could result in only 12 of the 25 being varied in the cutoff primary library. These primary library positions can then be recombined to form a secondary library, wherein all possible combinations of these variable positions form the secondary library. It should be noted that the non-variable positions are set to the reference sequence positions.

The formation of the secondary library using this method may be done in two general ways; either all variable positions are allowed to be any amino acid, or subsets of amino acids are allowed for each position.

In a preferred embodiment, all amino acid residues are allowed at each variable position identified in the primary library. That is, once the variable positions are identified, a secondary library comprising every combination of every amino acid at each variable position is made.

In a preferred embodiment, subsets of amino acids are chosen. The subset at any position may be either chosen by the user, or may be a collection of the amino acid residues generated in the primary screen. That is, assuming core residue 25 is variable and the primary screen gives 5 different possible amino acids for this position, the user may chose the set of good core residues outlined above (e.g. hydrophobic residues), or the user may build the set by chosing the 5 different amino acids generated in the primary screen. Alternatively, combinations of these techniques may be used, wherein the set of identified residues is manually expanded. For example, in some embodiments, fewer than the number of amino acid residues is chosen; for example, only three of the five may be chosen. Alternatively, the set is manually expanded; for example, if the computation picks two different hydrophobic residues, additional choices may be added. Similarly, the set may be biased, for example either towards or away from the wild-type sequence, or towards or away from known domains, etc.

In addition, this may be done by analyzing the primary library to determine which amino acid positions in the scaffold protein have a high mutational frequency, and which positions have a low mutation frequency. The secondary library can be generated by randomizing the amino acids at the positions that have high numbers of mutations, while keeping constant the positions that do not have mutations above a certain frequency. For example, if the position has less than 20% and more preferably 10% mutations, it may be kept constant as the reference sequence position.

In a preferred embodiment, the secondary library is generated from a probability distribution table. As outlined herein, there are a variety of methods of generating a probability distribution table, including using PDA, sequence alignments, forcefield calculations such as SCMF calculations, etc. In addition, the probability distribution can be used to generate information entropy scores for each position, as a measure of the mutational frequency observed in the library.

In this embodiment, the frequency of each amino acid residue at each variable position in the list is identified. Frequencies can be thresholded, wherein any variant frequency lower than a cutoff is set to zero. This cutoff is preferably 1%, 2%, 5%, 10% or 20%, with 10% being particularly preferred. These frequencies are then built into the secondary library. That is, as above, these variable positions are collected and all possible combinations are generated, but the amino acid residues that "fill" the secondary library are utilized on a frequency basis. Thus, in a non-frequency based secondary library, a variable position that has 5 possible residues will have 20% of the proteins comprising that variable position with the first possible residue, 20% with the second, etc. However, in a frequency based secondary library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create secondary libraries as described herein. SCMF can be used in three ways: the frequencies of amino acids and rotamers for each amino acid are listed at each position; the probabilities are determined directly from SCMF (see Delarue et la. Pac. Symp. Biocomput. 109-21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered list of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53-70 (1995); all of which are expressly incorporated by reference. Similar methods include, but are not limited to, OPLS-AA (Jorgensen, et al., J. Am. Chem. Soc. (1996), v 118, pp 11225-11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (1993), v 2, pp1697-1714; Liwo, et al., Protein Science (1993), v 2, pp1715-1731; Liwo, et al., J. Comp. Chem. (1997), v 18, pp849-873; Liwo, et al., J. Comp. Chem. (1997), v 18, pp874-884; Liwo, et al., J. Comp. Chem. (1998), v 19, pp259-276; Forcefield for Protein Structure Prediction (Liwo, et al., Proc. Natl. Acad. Sci. USA (1999), v 96, pp5482-5485); ECEPP/3 (Liwo et al., J Protein Chem 1994 May; 13(4):375-80); AMBER 1.1 force field (Weiner, et al., J. Am. Chem. Soc. v106, pp765-784); AMBER 3.0 force field (U.C. Singh et al., Proc. Natl. Acad. Sci. USA. 82:755-759); CHARMM and CHARMM22 (Brooks, et al., J. Comp. Chem. v4, pp 187-217); cvff3.0 (Dauber-Osguthorpe, et al., (1988) Proteins: Structure, Function and Genetics, v4,pp3l-47); cff91 (Maple, et al., J. Comp. Chem. v15, 162-182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table can be obtained by a combination of sequence alignments and computational approaches. For example, one can add amino acids found in the alignment of homologous sequences to the result of the computation. Preferable one can add the wild type amino acid identity to the probability table if it is not found in the computation.

As will be appreciated, a secondary library created by recombining variable positions and/or residues at the variable position may not be in a rank-ordered list. In some embodiments, the entire list may just be made and tested. Alternatively, in a preferred embodiment, the secondary library is also in the form of a rank ordered list. This may be done for several reasons, including the size of the secondary library is still too big to generate experimentally, or for predictive purposes. This may be done in several ways. In one embodiment, the secondary library is ranked using the scoring functions of PDA to rank the library members. Alternatively, statistical methods could be used. For example, the secondary library may be ranked by frequency score; that is, proteins containing the most of high frequency residues could be ranked higher, etc. This may be done by adding or multiplying the frequency at each variable position to generate a numerical score. Similarly, the secondary library different positions could be weighted and then the proteins scored; for example, those containing certain residues could be arbitrarily ranked.

As outlined herein, secondary libraries can be generated in two general ways. The first is computationally, as above, wherein the primary library is further computationally manipulated, for example by recombining the possible variant positions and/or amino acid residues at each variant position or by recombining portions of the sequences containing one or more variant position. It may be ranked, as outlined above. This computationally-derived secondary library can then be experimentally generated by synthesizing the library members or nucleic acids encoding them, as is more fully outlined below. Alternatively, the secondary library is made experimentally; that is, nucleic acid recombination techniques are used to experimentally generate the combinations. This can be done in a variety of ways, as outlined below.

In a preferred embodiment, the different protein members of the secondary library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412-26 (1998), hereby expressly incorporated by reference.

In a preferred embodiment, particularly for longer proteins or proteins for which large samples are desired, the secondary library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 1. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the secondary library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutaions in the desired proportions.

The total number of oligonucleotides needed is a function of the number of positions being mutated and the number of mutations being considered at these positions:

(number of oligos for constant positions)+$M1+M2+M3+\ldots Mn$=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonuclotide primer, the clusters can be set to the "good" correlations, and eliminate the bad combinations that may decrease the effectiveness of the library. However, if the residues of the cluster are far apart in sequence, and thus will reside on different oligonuclotides for synthesis, it may be desirable to either set the residues to the "god" correlation, or eliminate them as variable residues entirely. In an alternative embodiment, the library may be generated in several steps, so that the cluster mutations only appear together. This procedure, i.e., the procedure of identifying mutation clusters and either placing them on the same oligonucleotides oreliminating them from the library or library generation in several steps preserving clusters, can considerably enrich the experimental library with properly folded protein. Identification of clusters can be carried out by a number of wasy, e.g. by using known pattern recognition methods, comparisons of frequencies of occurrence of mutations or by using energy analysis of the sequences to be experimentally generated (for example, if the energy of interaction is high, the positions are correlated). these correlations may be positional correlations (e.g. variable positions 1 and 2 always change together or never change together) or sequence correlations (e.g. if there is a residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in patter recognition; New York, Wiley-Interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with Neural networks in C++/Abhijit S. Pandya, Robert B. Macy. Boca Raton, Fla.: CRC Press, 1996; Handbook of pattern recognition and computer vision/edited by C. H. Chen, L. F. Pau, P. S. P. Wang. $2^{nd}$ ed. Signapore; River Edge, N.J.: World Scientific, c1999; Friedman, Introduction to Pattern Recognition: Statistical, Structural, Neural, and Fuzzy Logic Approaches; River Edge, N.J.: World Scientific, c1999, Series title: Serien a machine perception and artificial intelligence; vol. 32; all of which are expressly incorporated by reference. In addition programs used to search for consensus motifs can be used as well.

In addition, correlations and shuffling can be fixed or optimized by altering the design of the oligonucleotides; that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotides start and stop site options can be computationally modeled and ranked according to number of clusters that are represented on single oligos, or the percentage of the resulting sequences consistent with the predicted libarary of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotide of different lengths.

In a preferred embodiment, the secondary library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences can also be an artificial set; for example, from a probability table (for example generated using SCMF) or a Monte Carlo set. Similarly, the "family" can be the top 10 and the bottom 10 sequences, the top 100 sequences, etc. This may also be done using error-prone PCR.

Thus, in a preferred embodiment, in silico shuffling is done using the computational methods described therein. That is, starting with either two libraries or two sequences, random recombinations of the sequences can be generated and evaluated.

In a preferred embodiment, error-prone PCR is done to generate the secondary library. See U.S. Pat. Nos. 5,605,793, 5,811,238, and 5,830,721, all of which are hereby incorporated by reference. This can be done on the optimal sequence or on top members of the library, or some other artificial set or family. In this embodiment, the gene for the optimal sequence found in the computational screen of the primary library can be synthesized. Error prone PCR is then performed on the optimal sequence gene in the presence of oligonucleotides that code for the mutations at the variant positions of the secondary library (bias oligonucleotides). The addition of the oligonucleotides will create a bias favoring the incorporation of the mutations in the secondary library. Alternatively, only oligonucleotides for certain mutations may be used to bias the library.

In a preferred embodiment, gene shuffling with error prone PCR can be performed on the gene for the optimal sequence, in the presence of bias oligonucleotides, to create a DNA sequence library that reflects the proportion of the mutations found in the secondary library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions can be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild type gene or other gene can be used, as is schematically depicted in FIG. 5. In this embodiment, a starting gene is used; generally, although this is not required, the gene is the wild type gene. In some cases it may be the gene encoding the global optimized sequence, or any other sequence of the list. In this embodiment, oligonucleotides are used that correspond to the variant positions and contain the different amino acids of the secondary library. PCR is done using PCR primers at the termini, as is known in the art. This provides two benefits; the first is that this generally requires fewer oligonucleotides and can result in fewer errors. In addition, it has experimental advantages in that if the wild type gene is used, it need not be synthesized.

In a preferred embodiment genes are isolated from a number of different species, such as human, mouse, pig, rat and horse, that share varying degrees of amino acid identity and shuffled to create a DNA sequence library. For example, a gene from one species may share from between 55 to 85% amino acid identity with the same gene isolated from another species. Genes may be obtained from any number of species and shuffled to create new gene sequences or chimeric genes encoding novel proteins. As will be appreciated by those of skill in the art, these methods can be applied to individual genes, gene families or clusters of genes within operons.

Preferably, an individual gene is obtained from at least two different species. In this embodiment, the gene from one species is cloned into a vector to produce a template molecule comprising single stranded nucleic acid molecules. The DNA from the second species is cleaved into fragments. The resulting fragments are added to the template molecule under conditions that permit the fragments to anneal to the template molecule. Unhybridized termini are enzymatically removed. Gaps between hybridized fragments are filled using an appropriate enzyme, such as a polymerase and nicks sealed using a ligase. The chimeric gene can be amplified using suitable primers or other techniques that are well known to those of skill in the art.

In a preferred embodiment, sequences derived from introns are used to mediate specific cleavage and ligation of discontinuous nucleic acid molecules to create libraries of novel genes and gene products as described in U.S. Pat. Nos. 5,498,531, and 5,780,272, both of which are hereby expressly incorporated by reference in their entirety. In one embodiment, a library of ribonucleic acids encoding a novel gene product or novel gene products is created by mixing splicing constructs comprising an exon and 3' and 5' intron fragments. See U.S. Pat. No. 5,498,531.

In another embodiment, DNA sequence libraries are created by mixing DNA/RNA hybrid molecules that contain intron derived sequences that are used to mediate specific cleavage and ligation of the DNA/RNA hybrid molecules such that the DNA sequences are covalently linked to form novel DNA sequences as described in U.S. Pat. No. 6,150, 141, WO 00/40715 and WO 00/17342, all of which are hereby expressly incorporated by reference in their entirety.

In a preferred embodiment, a variety of additional steps may be done to one or more secondary libraries; for example, further computational processing can occur, secondary libraries can be recombined, or cutoffs from different secondary libraries can be combined. In a preferred embodiment, a secondary library may be computationally remanipulated to form an additional secondary library (sometimes referred to herein as "tertiary libraries"). For example, any of the secondary library sequences may be chosen for a second round of PDA, by freezing or fixing some or all of the changed positions in the first secondary library. Alternatively, only changes seen in the last probability distribution table are allowed. Alternatively, the stringency of the probability table may be altered, either by increasing or decreasing the cutoff for inclusion. Similarly, the secondary library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library can be generated from combining secondary libraries.

For example, a probability distribution table from a secondary library can be generated and recombined, whether computationally or experimentally, as outlined herein. A PDA secondary library may be combined with a sequence alignment secondary library, and either recombined (again, computationally or experimentally) or just the cutoffs from each joined to make a new tertiary library. The top sequences from several libraries can be recombined. Primary and secondary libraries can similarly be combined. Sequences from the top of a library can be combined with sequences from the bottom of the library to more broadly sample sequence space, or only sequences distant from the top of the library can be combined. Primary and/or secondary libraries that analyzed different parts of a protein can be combined to a tertiary library that treats the combined parts of the protein. These combinations can be done to analyze large proteins, especially large multidomain proteins or complete protoesomes.

In a preferred embodiment, a tertiary library can be generated using correlations in the secondary library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation. This correlation, or "cluster" of residues, may be both detected and used in a variety of ways. (For the generation of correlations, see the earlier cited art).

In addition, primary and secondary libraries can be combined to form new libraries; these can be random combinations or the libraries, combining the "top" sequences, or weighting the combinations (positions or residues from the first library are scored higher than those of the second library).

As outlined herein, any number of protein attributes may be altered in these methods, including, but not limited to, enzyme activity, stability, solubility, aggregation, binding affinity, binding specificity, substrate specificity, structural integrity, immunogenicity, toxicity, generate peptide and peptidomimmetic libraries, create new antibody CDR's, generate new DNA, RNA bindings, etc.

It should be noted that therapeutic proteins utilized in these methods will preferentially have residues in the hydrophobic cores screened, to prevent changes in the molecular surface of the protein that might induce immunogenic responses. Therapeutic proteins can also be designed in the region surrounding their binding sites to their receptors. Such a region can be defined, for example, by including in the design all residues within a certain distance, for example 4.5 Å of the binding site residues. This range can vary from 4 to 6-10 Å. This design will serve to improve activity and specificity.

In addition, a step method can be done; see Zhao et al., Nature Biotech. 16:258 (1998), hereby incorporated by reference.

In a preferred embodiment, the methods of the invention are used not on known scaffold proteins, but on random peptides, to search a virtual library for those sequences likely to adapt a stable conformation. As discussed above, there is a current benefit and focus on screening random peptide libraries to find novel binding/modulators. However, the sequences in these experimental libraries can be randomized at specific sites only, or throughout the sequence. The number of sequences that can be searched in these libraries grows exponentially with the number of positions that are randomized. Generally, only up to $10^{12}$-$10^{15}$ sequences can be contained in a library because of the physical constraints of laboratories (the size of the instruments, the cost of producing large numbers of biopolymers, etc.). Other practical considerations can often limit the size of the libraries to $10^6$ or fewer. These limits are reached for only 10 amino acid positions. Therefore, only a sparse sampling of sequences is possible in the search for improved proteins or peptides in experimental sequence libraries, lowering the chance of success and almost certainly missing desirable candidates. Because of the randomness of the changes in these sequences, most of the candidates in the library are not suitable, resulting in a waste of most of the effort in producing the library.

However, using the automated protein design techniques outlined herein, virtual libraries of protein sequences can be generated that are vastly larger than experimental libraries. Up to $10^{75}$ candidate sequences (or more) can be screened computationally and those that meet design criteria, which favor stable and functional proteins can be readily selected. An experimental library consisting of the favorable candidates found in the virtual library screening can then be generated, resulting in a much more efficient use of the experimental library and overcoming the limitations of random protein libraries. Thus, the methods of the invention allow the virtual screening of a set of random peptides for peptides likely to take on a particular structure, and thus eliminating the large number of unpreferred or unallowed conformations without having to make and test the peptides.

In addition, it is possible to randomize regions or domains of protein as well.

Thus, in a preferred embodiment, the invention provides libraries of completely defined set of variant scaffold proteins, wherein at least 85% of the possible members are in the library, with at least about 90% and 95% being particularly preferred. However, it is also possible that errors are introduced into the libraries experimentally, and thus the libraries contain preferably less than 25% non-defined (e.g. error) sequences; with less than 10%, less than 5% and less than 1% particularly preferred. Thus libraries that have all members as well as some error members, or some members as well as error members are included herein.

As mentioned above, two principle benefits come from the virtual library screening: (1) the automated protein design generates a list of sequence candidates that are favored to meet design criteria; it also shows which positions in the sequence are readily changed and which positions are unlikely to change without disrupting protein stability and function. An experimental random library can be generated that is only randomized at the readily changeable, non-disruptive sequence positions. (2) The diversity of amino acids at these positions can be limited to those that the automated design shows are compatible with these positions. Thus, by limiting the number of randomized positions and the number of possibilities at these positions, the number of wasted sequences produced in the experimental library is reduced, thereby increasing the probability of success in finding sequences with useful properties.

For example, the table below lists the 10 favored sequences candidates from the virtual screening of 12 positions in a protein. It shows that positions 9, 10 and 12 are most likely to have changes that do not disrupt the function of the protein, suggesting that a random experimental library that randomizes positions 9, 10 and 12 will have a higher fraction of desirable sequences. Also, the virtual library suggests that position 10 is most compatible with Ile or Phe residues, further limiting the size of the library and allowing a more complete screening of good sequences.

acids, to allow the formation of all or most of the possible combinations over the length of the nucleic acid, thus forming a library of randomized candidate nucleic acids.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of

|    | 1   | 2   | 3   | 4   | 5   | 6   | 7   | 8   | 9   | 10  | 11  | 12  |
|----|-----|-----|-----|-----|-----|-----|-----|-----|-----|-----|-----|-----|
| 1  | LEU | LEU | ILE | ILE | ALA | LEU | LEU | LEU | LEU | PHE | ALA | LEU |
| 2  | LEU | LEU | ILE | ILE | ALA | LEU | LEU | LEU | LEU | ILE | ALA | LEU |
| 3  | LEU | LEU | ILE | ILE | ALA | LEU | LEU | LEU | LEU | ILE | ALA | LEU |
| 4  | LEU | LEU | ILE | ILE | ALA | LEU | LEU | LEU | LEU | PHE | ALA | ILE |
| 5  | LEU | LEU | ILE | ILE | ALA | LEU | LEU | LEU | LEU | PHE | ALA | ILE |
| 6  | LEU | LEU | ILE | ILE | ALA | LEU | LEU | LEU | LEU | ILE | ALA | ILE |
| 7  | LEU | LEU | ILE | ILE | ALA | LEU | LEU | LEU | ILE | PHE | ALA | LEU |
| 8  | LEU | LEU | ILE | ILE | ALA | LEU | LEU | LEU | LEU | ILE | ALA | ILE |
| 9  | LEU | LEU | ILE | ILE | ALA | LEU | LEU | LEU | ILE | PHE | ALA | LEU |
| 10 | LEU | LEU | ILE | ILE | ALA | LEU | LEU | LEU | LEU | LEU | ALA | LEU |

The automated design method uses physical chemical criteria to screen sequences, resulting in sequences that are likely to be stable, structured, and that preserve function, if needed. Different design criteria can be used to produce candidate sets that are biased for properties such as charged, solubility, or active site characteristics (polarity, size), or are biased to have certain amino acids at certain positions. That is, the candidate bioactive agents and candidate nucleic acids are randomized, either fully randomized or they are biased in their randomization, e.g. in nucleotide/residue frequency generally or per position. By "randomized" or grammatical equivalents herein is meant that each nucleic acid and peptide consists of essentially random nucleotides and amino acids, respectively. Thus, any amino acid residue may be incorporated at any position. The synthetic process can be designed to generate randomized peptides and/or nucleic small peptides to have activity on intracellular signaling cascades. In addition, agonists and antagonists of any number of molecules may be used as the basis of biased randomization of candidate bioactive agents as well.

In general, the generation of a prescreened random peptide libraries may be described as follows.

Any structure, whether a known structure, for example a portion of a known protein, a known peptide, etc., or a synthetic structure, can be used as the backbone for PDA. For example, structures from X-ray crystallographic techniques, NMR techniques, de novo modelling, homology modelling, etc. may all be used to pick a backbone for which sequences are desired. Similarly, a number of molecules or protein domains are suitable as starting points for the generation of biased randomized candidate bioactive agents.

A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

Thus, in general, known peptide ligands can be used as the starting backbone for the generation of the primary library.

In addition, structures known to take on certain conformations may be used to create a backbone, and then sequences screened for those that are likely to take on that conformation. For example, there are a wide variety of "ministructures" known, sometimes referred to as "presentation structures", that can confer conformational stability or give a random sequence a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Thus, synthetic presentation structures, i.e. artificial polypeptides, are capable of presenting a randomized peptide as a conformationally-restricted domain. Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362-2373 (1994), hereby incorporated by reference, and FIG. 3). Using this system investigators have isolated peptides capable of high affinity interaction with the appropriate target. In general, coiled-coil structures allow for between 6 to 20 randomized positons; (see Martin et al., EMBO J. 13(22):5303-5309 (1994), incorporated by reference).

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649-59 (1994) and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

Once the backbone is chosen and the primary library of the random peptides generated as outlined above, the secondary library generation and creation proceeds as for the known scaffold protein, including recombination of variant positions and/or amino acid residues, either computationally or experimentally. Again, libraries of DNA expressing the protein sequences defined by the automated protein design methods can be produced. Codons can be randomized at only the nucleotide sequence triplets that define the residue positions specified by the automated design method. Also, mixtures of base triplets that code for particular amino acids could be introduced into the DNA synthesis reaction to attach a full triplet defining an amino acid in one reaction step. Also, a library of random DNA oligomers could be designed that biases the desired positions toward certain amino acids, or that restricts those positions to certain amino acids. The amino acids biased for would be those specified in the virtual screening, or a subset of those.

Multiple DNA libraries are synthesized that code for different subsets of amino acids at certain positions, allowing generation of the amino acid diversity desired without having to fully randomize the codon and thereby waste sequences in the library on stop codons, frameshifts, undesired amino acids, etc. This can be done by creating a library that at each position to be randomized is only randomized at one or two of the positions of the triplet, where the position(s) left constant are those that the amino acids to be considered at this position have in common. Multiple DNA libraries would be created to insure that all amino acids desired at each position exist in the aggregate library. Alternatively, "shuffling", as is generally known in the art, can be done with multiple libraries. In addition, in silico shuffling can also be done.

Alternatively, the random peptide libraries may be done using the frequency tabulation and experimental generation methods including multiplexed PCR, shuffling, etc.

There are a wide variety of experimental techniques that can be used to experimentally generate the libraries of the invention, including, but not limited to, Rachitt-Enchira (http://www.enchira.com/gene_shuffling.htm); error-prone PCR, for example using modified nucleotides; known mutagenesis techniques including the use of multi-cassettes; DNA shuffling (Crameri, et al., Nature 391(6664):288-291. (1998)); heterogeneous DNA samples (U.S. Pat. No. 5,939, 250);

ITCHY (Ostermeier, et al., Nat Biotechnol 17(12):1205-1209. (1999)); StEP (Zhao, et al., Nat Biotechnol 16(3):258-261. (1998)), GSSM (U.S. Pat. No. 6,171,820,U.S. Pat. No. 5965408); in vivo homologous recombination, ligase assisted gene assembly, end-complementary PCR, profusion (Roberts and Szostak, Proc Natl Acad Sci USA 94(23): 12297-12302. (1997)); yeast/bacteria surface display (Lu, et al., Biotechnology (NY) 13(4):366-372. (1995); Seed and Aruffo, Proc Natl Acad Sci USA 84(10):3365-3369. (1987); Boder and Wittrup, Nat Biotechnol 15(6):553-557. (1997)).

Using the nucleic acids of the present invention which encode library members, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the library protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the library protein, as will be appreciated by those in the art; for example, transcriptional and translational regulatory nucleic acid sequences from Bacillus are preferably used to express the library protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences include constitutive and inducible promoter sequences. The promoters may be either naturally occurring promoters, hybrid or synthetic promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors and appropriate selection and screening protocols are well known in the art and are described in e.g., Mansour et al., *Cell,* 51:503 (1988) and Murray, *Gene Transfer and Expression Protocols, Methods in Molecular Biology, Vol.* 7 (Clifton: Humana Press, 1991).

In addition, in a preferred embodiment, the expression vector contains a selection gene to allow the selection of transformed host cells containing the expression vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that confers resistance to a selection agent. Suitable selection agents include, but are not limited to, neomycin (or its analog G418), blasticidin S, histinidol D, bleomycin, puromycin, hygromycin B, and other drugs.

In a preferred embodiment, the expression vector contains a RNA splicing sequence upstream or downstream of the gene to be expressed in order to increase the level of gene expression. See Barret et al., Nucleic Acids Res. 1991; Groos et al., Mol. Cell. Biol. 1987; and Budiman et al., Mol. Cell. Biol. 1988.

A preferred expression vector system is a retroviral vector system such as is generally described in Mann et al., Cell, 33:153-9 (1993); Pear et al., Proc. Natl. Acad. Sci. U.S.A., 90(18):8392-6 (1993); Kitamura et al., Proc. Natl. Acad. Sci. U.S.A., 92:9146-50 (1995); Kinsella et al., Human Gene Therapy, 7:1405-13; Hofmann et al., Proc. Natl. Acad. Sci. U.S.A., 93:5185-90; Choate et al., Human Gene Therapy, 7:2247 (1996); PCT/US97/01019 and PCT/US97/01048, and references cited therein, all of which are hereby expressly incorporated by reference.

The library proteins of the present invention are produced by culturing a host cell transformed with nucleic acid, preferably an expression vector, containing nucleic acid encoding an library protein, under the appropriate conditions to induce or cause expression of the library protein. As outlined below, the libraries can be the basis of a variety of display techniques, including, but not limited to, phage and other viral display technologies, yeast, bacterial, and mammalian display technologies. The conditions appropriate for library protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

As will be appreciated by those in the art, the type of cells used in the present invention can vary widely. Basically, a wide variety of appropriate host cells can be used, including yeast, bacteria, archaebacteria, fungi, and insect and animal cells, including mammalian cells. Of particular interest are *Drosophila melanogaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. See the ATCC cell line catalog, hereby expressly incorporated by reference. In addition, the expression of the secondary libraries in phage display systems, such as are well known in the art, are particularly preferred, especially when the secondary library comprises random peptides. In one embodiment, the cells may be genetically engineered, that is, contain exogenous nucleic acid, for example, to contain target molecules.

In a preferred embodiment, the library proteins are expressed in mammalian cells. Any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a random library member. As is more fully described below, cell types implicated in a wide variety of disease conditions are particularly useful, so long as a suitable screen may be designed to allow the selection of cells that exhibit an altered phenotype as a consequence of the presence of a library member within the cell.

Accordingly, suitable mammalian cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

Mammalian expression systems are also known in the art, and include retroviral systems. A mammalian promoter is any DNA sequence capable of binding mammalian RNA polymerase and initiating the downstream (3') transcription of a coding sequence for library protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, library proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of library protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the library protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cell using techniques well known in the art, such as calcium chloride treatment, electroporation, and others.

In one embodiment, library proteins are produced in insect cells. Expression vectors for the transformation of insect cells, and in particular, baculovirus-based expression vectors, are well known in the art and are described e.g., in O'Reilly et al., *Baculovirus Expression Vectors: A Laboratory Manual* (New York: Oxford University Press, 1994).

In a preferred embodiment, library protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The library protein may also be made as a fusion protein, using techniques well known in the art. Thus, for example, for the creation of monoclonal antibodies, if the desired epitope is small, the library protein may be fused to a carrier protein to form an immunogen. Alternatively, the library protein may be made as a fusion protein to increase expression, or for other reasons. For example, when the library protein is an library peptide, the nucleic acid encoding the peptide may be linked to other nucleic acid for expression purposes. Similarly, other fusion partners may be used, such as targeting sequences which allow the localization of the library members into a subcellular or extracellular compartment of the cell, rescue sequences or purification tags which allow the purification or isolation of either the library protein or the nucleic acids encoding them; stability sequences, which confer stability or protection from degradation to the library protein or the nucleic acid encoding it, for example resistance to proteolytic degradation, or combinations of these, as well as linker sequences as needed.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the library member comprises a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the library member or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: $MG(X)_nGGPP$, where X is any amino acid and n is an integer of at least four.

In one embodiment, the library nucleic acids, proteins and antibodies of the invention are labeled. By "labeled" herein is meant that nucleic acids, proteins and antibodies of the invention have at least one element, isotope or chemical compound attached to enable the detection of nucleic acids, proteins and antibodies of the invention. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the library protein is purified or isolated after expression. Library proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the library protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the library protein. In some instances no purification will be necessary.

Once expressed and purified if necessary, the library proteins and nucleic acids are useful in a number of applications.

In general, the secondary libraries are screened for biological activity. These screens will be based on the scaffold protein chosen, as is known in the art. Thus, any number of protein activities or attributes may be tested, including its binding to its known binding members (for example, its substrates, if it is an enzyme), activity profiles, stability profiles (pH, thermal, buffer conditions), substrate specificity, immunogenicity, toxicity, etc.

When random peptides are made, these may be used in a variety of ways to screen for activity. In a preferred embodiment, a first plurality of cells is screened. That is, the cells into which the library member nucleic acids are introduced are screened for an altered phenotype. Thus, in this embodiment, the effect of the library member is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the secondary library, i.e. a different library member, although as will be appreciated by those in the art, some cells within the library may not contain one and and some may contain more than one. When methods other than retroviral infection are used to introduce the library members into a plurality of cells, the distribution of library members within the individual cell members of the cellular library may vary widely, as it is generally difficult to control the number of nucleic acids which enter a cell during electroporation, etc.

In a preferred embodiment, the library nucleic acids are introduced into a first plurality of cells, and the effect of the library members is screened in a second or third plurality of cells, different from the first plurality of cells, i.e. generally a different cell type. That is, the effect of the library member is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the library members (for example, when inducible promoters are used), to produce the library proteins.

Thus, in one embodiment, the methods of the present invention comprise introducing a molecular library of library members into a plurality of cells, a cellular library. The plurality of cells is then screened, as is more fully outlined below, for a cell exhibiting an altered phenotype. The altered phenotype is due to the presence of a library member.

In a preferred embodiment, the libraries are used in any number of display techniques. For example, the libraries may be displayed using phage or enveloped virus systems, bacterial systems, yeast two hybrid systems or mammalian systems.

In a preferred embodiment, the libraries are displayed using a phage or enveloped virus system. For example, a library of viruses, each carrying a distinct peptide sequence as part of the coat protein, can be produced by inserting random oligonucleotides sequences into the coding sequence of viral coat or envelope proteins. Several different viral systems have been used to display peptides, as described in Smith, G. P, (1985) *Science,* 228:1315-1317; Santini, C., et al., (1998) *J. Mol. Biol.,* 282:125-135; Sternberg, N. and Hoess, R. H. (1995) *Proc. Natl. Acad. Sci. USA,* 92:1609-1613; Maruyama, I. N., et al. (1994) *Proc. Natl. Acad. Sci. USA,* 91:8273-8277; Dunn, I. S., (1995) *J. Mol. Biol.,* 248:497-506; Rosenberg, A., et al. (1996) *Innovations* 6:1-6); Ren, Z. J., et al. (1996) *Protein Sci.,* 5:1833-1843; Efimov, V. P., et al. (1995) *Virus Genes* 10:173-177; Dulbecco, R., U.S. Pat. No. 4,593,002; Ladner, R. C., et al., U.S. Pat. No. 5,837,500; Ladner, R. C., et al., U.S. Pat. No. 5,223,409; Dower, et al., U.S. Pat. No. 5,427,908; Russell et al., U.S. Pat. No. 5,723,287; Li U.S. Pat. No. 6,190,856; and the application entitled "METHODS AND COMPOSITIONS FOR THE CONSTRUCTION AND USE OF ENVELOPE VIRUSES AS DISPLAY PARTICLES", filed Aug. 2, 2001, serial number not yet assigned, all of which are expressly incorporated by reference.

In a preferred embodiment, the libraries are displayed on the surface of a bacterial cell as is described in WO 97/37025, which is expressly incorporated by reference in its entirety. In this embodiment, surface anchoring vectors are provided for the surface expression of genes encoding proteins of interest. At a minima the vector includes a gene encoding an ice nucleation protein, a secretion signal a targeting signal and a gene of interest. Preferably, the bacterial host is a gram negative bacterium belonging to the genera Escherichia, Acetobacter, Pseudomonas, Xanthomonas, Erwinia, and Xymomonas. Advantages to using the ice nucleation protein as the surface anchoring protein are the high level of expression of the ice nucleation protein on the surface of the bacterial cell and its stable expression during the stationary phase of bacterial cell growth.

In a preferred embodiment, the libraries are displayed using yeast two hybrid systems as is described in Fields and Song (1989) *Nature* 340:245, which is expressly incorporated herein by reference. Yeast-based two-hybrid systems utilize chimeric genes and detect protein-protein interactions via the activation of reporter-gene expression. Reporter-gene expression occurs as a result of reconstitution of a functional transcription factor caused by the association of fusion proteins encoded by the chimeric genes. Preferably, the yeast two-hybrid system commercially available from Clontech is used to screen libraries for proteins that interact with a candidate proteins. See generally, Ausubel et al., Current Protocols in Molecular Biology, John Wiley & Sons, pp. 13.14.1-13.14.14, which is expressly incorporated herein by reference.

In a preferred embodiment, the libraries are displayed using mammalian systems. For example, a cell-based display can be used to display large cDNA libraries in mammalian cells as described in Nolan, et al., U.S. Pat. No. 6,153,380; Shioda, et al. U.S. Pat. No. 6,251,676, both of which are expressly incorporated herein by reference.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in phosphorylation; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens; etc. By "capable of altering the phenotype" herein is meant that the library member can change the phenotype of the cell in some detectable and/or measurable way.

The altered phenotype may be detected in a wide variety of ways, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the randomized nucleic acid was introduced; in other embodiments, the altered phenotype is detected in a second cell which is responding to some molecular signal from the first cell.

In a preferred embodiment, the library member is isolated from the positive cell. This may be done in a number of ways. In a preferred embodiment, primers complementary to DNA regions common to the constructs, or to specific components of the library such as a rescue sequence, defined above, are used to "rescue" the unique random sequence. Alternatively, the member is isolated using a rescue sequence. Thus, for example, rescue sequences comprising epitope tags or purification sequences may be used to pull out the library member, using immunoprecipitation or affinity columns. In some instances, this may also pull out things to which the library member binds (for example the primary target molecule) if there is a sufficiently strong binding interaction between the library member and the target molecule. Alternatively, the peptide may be detected using mass spectroscopy.

Once rescued, the sequence of the library member is determined. This information can then be used in a number of ways.

In a preferred embodiment, the member is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of the member is used to generate more libraries, as outlined herein.

In a preferred embodiment, the library member is used to identify target molecules, i.e. the molecules with which the member interacts. As will be appreciated by those in the art, there may be primary target molecules, to which the library member binds or acts upon directly, and there may be secondary target molecules, which are part of the signalling pathway affected by the library member; these might be termed "validated targets".

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable library member is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the library may be put onto a chip or substrate as an array to make a "protein chip" or "biochip" to be used in high-throughput screening (HTS) techniques. Thus, then invention provides substrates with arrays comprising libraries (generally secondary or tertiary libraries" of proteins.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used. Similarly, the arrays may be placed on the inside surface of a tube, for flow-through sample analysis to minimize sample volume.

By "array" herein is meant a plurality of library members in an array format; the size of the array will depend on the composition and end use of the array. Arrays containing from about 2 different library members to many thousands can be made. Generally, the array will comprise from $10^2$ to $10^8$ different proteins (all numbers are per square centimeter), with from about $10^3$ to about $10^6$ being preferred and from about $10^3$ to $10^5$ being particularly preferred. In addition, in some arrays, multiple substrates may be used, either of different or identical compositions. Thus for example, large arrays may comprise a plurality of smaller substrates.

As will be appreciated by those in the art, the library members may either be synthesized directly on the substrate, or they may be made and then attached after synthesis. In a preferred embodiment, linkers are used to attach the proteins to the substrate, to allow both good attachment, sufficient flexibility to allow good interaction with the target molecule, and to avoid undesirable binding reactions.

In a preferred embodiment, the library members are synthesized first, and then covalently or otherwise immobilized to the substrate. This may be done in a variety of ways, including known spotting techniques, ink jet techniques, etc.

As will be appreciated by those in the art, the proteinaceous library members may be attached to the substrate in a wide variety of ways. The functionalization of solid support surfaces such as certain polymers with chemically reactive groups such as thiols, amines, carboxyls, etc. is generally known in the art. Accordingly, substrates may be used that have surface chemistries that facilitate the attachment of the desired functionality by the user. Some examples of these surface chemistries include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different libraries to the substrates, generally using known chemistries. For example, libraries containing carbohydrates may be attached to an amino-functionalized support; the aldehyde of the carbohydrate is made using standard techniques, and then the aldehyde is reacted with an-amino group on the surface. In an alternative embodiment, a sulfhydryl linker may be used. There are a number of sulfhydryl reactive linkers known n the art such as SPDP, maleimides, a-haloacetyls, and pyridyl disulfides (see for example the 1994 Pierce Chemical Company catalog, technical section on cross-linkers, pages 155-200, incorporated herein by reference) which can be used to attach cysteine containing members to the support. Alternatively, an amino group on the library member may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the protein) nay be derivatized using well known linkers (see the Pierce catalog). For example, carbodiimides activate carboxyl groups for attack by good nucleophiles such as amines (see Torchilin et al., Critical (Rev.

Therapeutic Drug Carrier Systems, 7(4):275-308 (1991), expressly incorporated herein). In addition, library proteins may also be attached using other techniques known in the art, for example for the attachment of antibodies to polymers; see Slinkin et al., Bioconj. Chem. 2:342-348 (1991); Torchilin et al., supra; Trubetskoy et al., Bioconj. Chem. 3:323-327 (1992); King et al., Cancer Res. 54:6176-6185 (1994); and Wilbur et al., Bioconjugate Chem. 5:220-235 (1994), all of which are hereby expressly incorporated by reference). Similarly, when the library members are made recombinantly, the use of epitope tags (FLAG, etc.) or His6 tags allow the attachment of the members to the surface i.e. with antibody coated surfaces, metal (Ni) surfaces, etc.). In addition, labeling the library members with biotin or other binding partner pairs allows the use of avidin coated surfaces, etc. It should be understood that the proteins may be attached in a variety of ways, including those listed above. What is important is that manner of attachment does not significantly alter the functionality of the protein; that is, the protein should be attached in such a flexible manner as to allow its interaction with a target.

Once the biochips are made, they may be used in any number of formats for a wide variety of purposes, as will be appreciated by those in the art. For example, the scaffold protein serving as the library starting point may be an enzyme; by putting libraries of variants on a chip, the variants can be screened for increased activity by adding substrates, or for inhibitors. Similarly, variant libraries of ligand scaffolds can be screened for increased or decreased binding affinity to the binding partner, for example a cell surface receptor. Thus, in this embodiment, for example, the extracellular portion of the receptor can be added to the array and binding affinity tested under any number of conditions; for example, binding and/or activity may be tested under different pH conditions, different buffer, salt or reagent concentrations, different temperatures, in the presence of competitive binders, etc.

Thus, in a preferred embodiment, the methods comprise differential screening to identity bioactive gents that are capable of either binding to the variant proteins and/or modulating the activity of the variant proteins. "Modulation" in this context includes both an increase in activity (e.g. enzymatic activity or binding affinity) and a decrease.

Another preferred embodiment utilizes differential screening to identify drug candidates that bind to the native protein, but cannot bind to modified proteins.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined.

A variety of other reagents may be included in the screening assays. These include reagents like salts, neutral proteins, e.g. albumin, detergents, etc. which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In a preferred embodiment, the activity of the variant protein is increased; in another preferred embodiment, the activity of the variant protein is decreased. Thus, bioactive agents that are antagonists are preferred in some embodiments, and bioactive agents that are agonists may be preferred in other embodiments.

Thus, in a preferred embodiment, the biochips comprising the secondary or tertiary libraries are used to screen candidate agents for binding to library members. By "candidate bioactive agent" or "candidate drugs" or grammatical equivalents herein is meant any molecule, e.g. proteins (which herein includes proteins, polypeptides, and peptides), small organic or inorganic molecules, polysaccharides, polynucleotides, etc. which are to be tested against a particular target. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate agents, including the wide variety of known combinatorial chemistry-type libraries.

In a preferred embodiment, candidate agents are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate bioactive agents prior to the assay; only candidate agents that bind to the target need be identified. In addition, as is known in the art, coding tags using split synthesis reactions may be done, to essentially identify the chemical moieties on the beads.

Alternatively, a preferred embodiment utilizes libraries of natural compounds in the form of bacterial, fungal, plant and animal extracts that are available or readily produced, and can be attached to beads as is generally known in the art.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate bioactive agents include proteins, nucleic acids, and chemical moieties.

In a preferred embodiment, the candidate bioactive agents are proteins. In a preferred embodiment, the candidate bioactive agents are naturally occurring proteins or fragments of naturally occurring proteins. Thus, for example, cellular extracts containing proteins, or random or directed digests of proteinaceous cellular extracts, may be attached to beads as is more fully described below. In this way libraries of procaryotic and eucaryotic proteins may be made for screening against any number of targets. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents. In addition, the candidate agents may themselves be the product of the invention; that is, a library of proteinaceous candidate agents may be made using the methods of the invention.

The library should provide a sufficiently structurally diverse population of randomized agents to effect a probabilistically sufficient range of diversity to allow binding to a particular target. Accordingly, an interaction library must be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$-$10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$-$10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

Thus, in a preferred embodiment, the invention provides biochips comprising libraries of variant proteins, with the library comprising at least about 100 different variants, with at least about 500 different variants being preferred, about 1000 different variants being particularly preferred and about 5000-10,000 being especially preferred.

In one embodiment, the candidate library is fully randomized, with no sequence preferences or constants at any position. In a preferred embodiment, the candidate library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules.

For example, when the candidate bioactive agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

Thus, a number of molecules or protein domains are suitable as starting points for the generation of biased randomized candidate bioactive agents. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 (1986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoramidite linkages (see Eckstein, Oligonucleotides and Analogues: A Practical approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995)); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am.

Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the candidate bioactive agents are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, aeterocyclic compounds (including purines, pyrimidines, benzodiazepins, beta-lactams, tetracylines, ephalosporins, and carbohydrates), steroids (including estrogens, androgens, cortisone, ecodysone, atc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate agent at a time. Thus, the library of candidate agents used in any particular assay may include only one type of agent (i.e. peptides), or multiple types (peptides and organic agents).

Thus, in a preferred embodiment, the invention provides biochips comprising variant libraries of at east one scaffold protein, and methods of screening utilizing the biochips. Thus, for example, the invention provides completely defined libraries of variant scaffold proteins having a defined set number, wherein at least 85-90-95% of the possible members are present in the library.

I addition, as will also be appreciated by those in the art, the biochips of the invention may be part of HTS system utilizing any number of components. Fully robotic or microfluidic systems include automated liquid-, particle-, cell- and organism-handling including high throughput pipetting to perform all steps of gene targeting and recombination applications. This includes liquid, particle, cell, and organism manipulations such as aspiration, dispensing, mixing, diluting, washing, accurate volumetric transfers; retrieving, and discarding of pipes tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

The system used can include a computer workstation comprising a microprocessor programmed to manipulate a device selected from the group consisting of a thermocycler, a multichannel pipettor, a sample handler, a plate handler, a gel loading system, an automated transformation system, a gene sequencer, a colony picker, a bead picker, a cell sorter, an incubator, a light microscope, a fluorescence microscope, a spectrofluorimeter, a spectrophotometer, a luminometer, a CCD camera nd combinations thereof.

In a preferred embodiment, the methods of the invention are used to generate variant libraries to facilitate and correlate single nucleotide polymorphism (SNP) analysis. That is, by drawing on known SNP data and determining the effect of the SNP on the protein, information concerning SNP analysis can be determined. Thus, for example, making a "sequence alignment" of sorts using known SNPs can result in a probability distribution table that can be used to design all possible SNP variants, which can then be put on a biochip and tested for activity and effect.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Computational Prescreening on β-lactamase TEM-1

Preliminary experiments were performed on the β-lactamase gene TEM-1. Brookhaven Protein Data Bank entry 1BTL was used as the starting structure. All water molecules and the $SO_4^{2-}$ group were removed and explicit hydrogens were generated on the structure. The structure was then minimized for 50 steps without electrostatics using the conjugate gradient method and the Dreiding II force field. These steps were performed using the BIOGRAF program (Molecular Simulations, Inc., San Diego, Calif.). This minimized structure served as the template for all the protein design calculations.

Computational Pre-Screening

Computational pre-screening of sequences was performed using PDA. A 4 Å sphere was drawn around the heavy side chain atoms of the four catalytic residues (S70, K73, S130, and E166) and all amino acids having heavy side chain atoms within this distance cutoff were selected. This yielded the following 7 positions: F72, Y105, N132, N136, L169, N170, and K234. Two of these residues, N132 and K234, are highly conserved across several different β-lactamases and were therefore not included in the design, leaving five variable positions (F72, Y105, N136, L169, N170). These designed positions were allowed to change their identity to any of the 20 naturally occurring amino acids except proline, cysteine, and glycine (a total of 17 amino acids). Proline is usually not allowed since it is difficult to define appropriate rotamers for proline, cysteine is excluded to prevent formation of disulfide bonds, and glycine is excluded because of conformational flexibility.

Additionally, a second set of residues within 5 Å of the residues selected for PDA design were floated (their amino acid identity was retained as wild type, but their conformation was allowed to change). The heavy side chain atoms were again used to determine which residues were within the cutoff. This yielded the following 28 positions: M68, M69, S70, T71, K73, V74, L76, V103, E104, S106, P107, I127, M129, S130, A135, L139, L148, L162, R164, W165, E166, P167, D179, M211, D214, V216, S235, I247. A248 was included as a floated position instead of I247. The two prolines, P107 and P167, were excluded from the floated residues, as were positions M69, R164, and W165, since their crystal structures exhibit highly strained rotamers, leaving 23 floated residues from the second set. The conserved residues N132 and K234 from the first sphere (4 Å) were also floated, resulting in a total of 25 floated residues.

The potential functions and parameters used in the PDA calculations were as follows. The van der Waals scale factor was set to 0.9, and the electrostatic potential was calculated using a distance attenuation and a dielectric constant of 40. The well depth for the hydrogen bond potential was set to 8 kcal/mol with a local and remote backbone scale factor of 0.25 and 1.0 respectively. The solvation potential was only calculated for designed positions classified as core (F72, L169, M68, T71, V74, L76, I127, A135, L139, L148, L162, M211 and A248). Type 2 solvation was used (Street and Mayo, 1998). The non-polar exposure multiplication factor was set to 1.6, the non-polar burial energy was set to 0.048 kcal/mol/Å$^2$, and the polar hydrogen burial energy was set to 2.0 kcal/mol.

The Dead End Elimination (DEE) optimization method (see reference) was used to find the lowest energy, ground state sequence. DEE cutoffs of 50 and 100 kcal/mol were used for singles and doubles energy calculations, respectively.

Starting from the DEE ground state sequence, a Monte Carlo (MC) calculation was performed that generated a list of the 1000 lowest energy sequences. The MC parameters were 100 annealing cycles with 1,000,000 steps per cycle. The non-productive cycle limit was set to 50. In the annealing schedule, the high and low temperatures were set to 5000 and 100 K respectively.

The following probability distribution was then calculated from the top 1000 sequences in the MC list (see Table 3 below). It shows the number of occurrences of each of the amino acids selected for each position (the 5 variable positions and the 25 floated positions).

TABLE 3

Monte Carlo analysis (amino acids and their number of occurrences (for the top 1000 sequences).

| Position | Amino acid occurrences |
|---|---|
| 68 | M: 1000 |
| 70 | S: 1000 |
| 71 | T: 1000 |
| 72 | Y: 591 F: 365 V: 35 E: 8 L: 1 |
| 73 | K: 1000 |
| 74 | V: 1000 |
| 76 | L: 1000 |
| 103 | V: 1000 |
| 104 | E: 1000 |
| 105 | M: 183 Q: 142 I: 132 N: 129 E: 126 S: 115 D: 97 A: 76 |
| 106 | S: 1000 |
| 127 | I: 1000 |
| 129 | M: 1000 |
| 130 | S: 1000 |
| 132 | N: 1000 |
| 135 | A: 1000 |
| 136 | D: 530 M: 135 N: 97 V: 68 E: 66 S: 38 T: 33 A: 27 Q: 6 |
| 139 | L: 1000 |
| 148 | L: 1000 |
| 162 | L: 1000 |
| 166 | E: 1000 |
| 169 | L: 689 E: 156 M: 64 S: 37 D: 23 A: 21 Q: 10 |
| 170 | M: 249 L: 118 E: 113 D: 112 T: 90 Q: 87 S: 66 R: 44 A: 35 N: 24 F: 21 K: 15 Y: 9 H: 9 V: 8 |
| 179 | D: 1000 |
| 211 | M: 1000 |
| 214 | D: 1000 |
| 216 | V: 1000 |
| 234 | K: 1000 |
| 235 | S: 1000 |
| 248 | A: 1000 |

This probability distribution was then transformed into a rounded probability distribution (see Table 4). A 10% cutoff value was used to round at the designed positions and the wild type amino acids were forced to occur with a probability of at least 10%. An E was found at position 169 15.6% of the time. However, since this position is adjacent to another designed position, 170, its closeness would have required a more complicated oligonucleotide library design; E was therefore not included for this position when generating the sequence library (only L was used).

TABLE 4

PDA probability distribution for the designed positions of β-lactamase (rounded to the nearest 10%).

| 72 | 105 | 136 | 169 | 170 |
|---|---|---|---|---|
| Y 50% | M 20% | D 70% | L 100% | M 30% |
| F 50% | Q 20% | M 20% | | L 20% |
| | I 20% | N 10% | | E 20% |
| | N 10% | | | D 20% |
| | E 10% | | | N 10% |
| | S 10% | | | |
| | Y 10% | | | |

As seen from Table 4, the computational pre-screening resulted in an enormous reduction in the size of the problem. Originally, 17 different amino acids were allowed at each of the 5 designed positions, giving $17^5$—1,419,857 possible sequences. This was pared down to just $2*7*3*1*5=210$ possible sequences—a reduction of nearly four orders of magnitude.

Generation of Sequence Library

Overlapping oligonucleotides corresponding to the full length TEM-1 gene for β-lacatamase and all desired mutations were synthesized and used in a PCR reaction as described previously (FIG. 1), resulting in a sequence library containing the 210 sequences described above.

Synthesis of Mutant TEM-1 Genes

To allow the mutation of the TEM-1 gene, pCR2.1 (Invitrogen) was digested with XbaI and EcoRI, blunt ended with T4 DNA polymerase, and religated. This removes the HindIII and XhoI sites within the polylinker. A new XhoI site was then introduced into the TEM-1 gene at position 2269 (numbering as of the original pCR2.1) using a Quick-changeSite-DirectedMutagenesis Kit as described by the manufacturer (Stratagene). Similarly, a new HindIII site was introduced at position 2674 to give pCR-Xen1.

To construct the mutated TEM-1 genes, overlapping 40meroligonucleotides were synthesized corresponding to the sequence between the newly introduced Xho1 and HindIII sites, designed to allow a 20 nucleotide overlap with adjacent oligonucleotides. At each of the designed positions (72, 105, 136 and 170) multiple oligonucleotides were synthesized,each containing a different mutation so that all the possible combinations of mutant sequences (210) could be made in the desired proportions as shown in Table 4. For example, at position 72, two sets of oligonucleotides were synthesized, one containing an F at position 72, the other containing a Y. Each oligonucleotide was resuspended at a concentration of 1 μg/μl, and equal molar concentrations of the oligonucleotides were pooled.

At the redundant positions, each oligonucleotide was added at a concentration that reflected the probabilities in Table 4. For example, at position 72 equal amounts of the two oligonucleotides were added to the pool, while at position 136, twice as much M-containing oligonucleotide was added compared to the N-containing oligonucleotide, and seven times as much D-containing oligonucleotide was added compared to the N-containing oligonucleotide.

DNA Library Assembly

For the first round of PCR, 2 μl of pooled oligonucleotides at the desired probabilities (Table 4) were added to a 100 μl reaction that contained 2 μl 10 mM dNTPs, 10 μl 10×Taq buffer (Qiagen), 1 μl of Taq DNA polymerase(5 units/μl: Qiagen) and 2 μl Pfu DNA polymerase(2.5 units/μl: Promega). The reaction mixture was assembled on ice and subjected to 94° C. for 5 minutes, 15 cycles of 94° C. for 30 seconds, 52° C. for 30 seconds and 72° C. for 30 seconds, and a final extension step of 72° C. for 10 minutes.

Isolation of Full Length Oligonucleotides

For the second round of PCR, 2.5 μl of the first round reaction was added to a 100 μl reaction containing 2 μl 10 mM dNTPs, 10 μl of 10×Pfu DNA polymerase buffer (Promega), 2 μl Pfu DNA polymerase (2.5 units/μl: Promega), and 1 μg of oligonucleotides corresponding to the 5' and 3' ends of the synthesized gene. The reaction mixture was assembled on ice and subjected to 94° C. for 5 minutes, 20 cycles of 94° C. for 30 seconds, 52° C. for 30 seconds and 72° C. for 30 seconds, and a final extension step of 72° C. for 10 minutes to isolate the full length oligonucleotides.

Purification of DNA Library

The PCR products were purified using a QIAquick PCR Purification Kit (Qiagen), digested with Xho1 and HindIII, electrophoresed through a 1.2% agarose gel and re-purified using a QIAquick Gel Extraction Kit (Qiagen).

Verification of Sequence Library Identity

The PCR products containing the library of mutant TEM-1 β-lactamase genes were then cloned between a promoter and terminator in a kanamycin resistant plasmid and transformed into E. coli. An equal number of bacteria were then spread onto media containing either kanamycin or ampicillin. All transformed colonies will be resistant to kanamycin, but only those with active mutated β-lactamase genes will grow on ampicillin. After overnight incubation, several colonies were observed on both plates, indicating that at least one of the above sequences encodes an active β-lactamase. The number of colonies on the kanamycin plate far outnumbered those on the ampicillin plate (roughly a 5:1 ratio) suggesting that either some of the sequences destroy activity, or that the PCR introduces errors that yield an inactive or truncated enzyme.

To distinguish between these possibilities, 60 colonies were picked from the kanamycin plate and their plasmid DNA was sequenced. This gave the distribution shown in Table 5.

TABLE 5

Percentages predicted by PDA vs. those observed from experiment for the designed positions.

| Wild Type | PDA Residues (Predicted Percentage/Observed Percentage) | | | | | |
|---|---|---|---|---|---|---|
| 72F | Y 50/50 | F 50/50 | | | | |
| 105Y | M 20/27 | Q 20/18 | I 20/21 | N 10/7 | E 10/7 | S 10/10 Y 10/10 |
| 136N | D 70/72 | M 20/17 | N 10/11 | | | |
| 170N | M 30/34 | L 20/21 | E 20/21 | D 20/17 | N 10/7 | |

Note that the observed percentages of each amino acid at all four positions closely match the predicted percentages. Sequencing also revealed that only one of the 60 colonies contained a PCR error, a G to C transition.

This small test demonstrates that multiple PCR with pooled oligonucleotides can be used to construct a sequence library that reflects the desired proportions of amino acid changes.

Experimental Screening of Sequence Library

The purified PCR product containing the library of mutated sequences was then ligated into pCR-Xen1 that had previously been digested with Xho1 and HindIII and purified. The ligation reaction was transformed into competent TOP10 E. coli cells (Invitrogen). After allowing the cells to recover for 1 hour at 37° C., the cells were spread onto LB plates containing the antibiotic cefotaxime at concentrations ranging from 0.1 μg/ml to 50 μg/ml and selected for increasing resistance.

matic activity. These positions were treated as wild type residues, which means that their conformation was allowed to change but not their amino acid identity (see FIG. 2).

Three of the 20 naturally occurring amino acids were not considered (cysteine, proline, and glycine). Therefore, 17 different amino acids were still possible at the remaining 19 positions; the problem yields $17^{19}=2.4\times10^{23}$ different amino acid sequences. This number is 10 orders of magnitude larger than what can be handled by state of the art directed evolution methods. Clearly these approaches cannot be used to screen the complete dimensionality of the problem and consider all sequences with multiple substitutions. Therefore PDA calculations were performed to reduce the search space. A list of the 10,000 lowest energy sequences was created and the probability for each amino acid at each position was determined(see Table 1).

TABLE 1

Probability of amino acids at the designed positions resulting from the PDA calculation of the wild type (WT) enzyme structure. Only amino acids with a probability greater than 1% are shown.

| WT | PDA Probability Distribution | | | | | | |
|---|---|---|---|---|---|---|---|
| 5 Y | W 37.2% | F 25.8% | Y 22.9% | H 14.0% | | | |
| 7 Q | E 69.1% | L 30.2% | | | | | |
| 11 D | I 41.2% | D 10.7% | V 10.1% | M 7.9% | L 6.4% | E 5.3% | T 4.2% |
| | Q 3.8% | Y 2.6% | F 2.1% | N 1.9% | S 1.9% | A 1.1% | |
| 37 V | D 29.9% | M 29.4% | V 21.4% | S 12.8% | I 4.1% | E 1.0% | |
| 39 G | A 99.8% | | | | | | |
| 63 N | W 91.2% | Q 6.7% | A 1.4% | | | | |
| 65 Y | E 91.7% | L 4.9% | M 3.4% | | | | |
| 67 T | E 81.0% | D 12.3% | L 3.9% | A 1.7% | | | |
| 71 W | V 37.8% | F 25.5% | W 8.5% | M 6.0% | D 5.8% | E 4.3% | I 1.0% |
| 80 Y | M 32.4% | L 31.5% | F 19.0% | I 5.9% | Y 5.7% | E 3.7% | |
| 82 V | V 88.6% | D 11.0% | | | | | |
| 88 Y | N 91.1% | K 6.6% | W 1.3% | | | | |
| 110 T | D 99.9% | | | | | | |
| 115 A | A 35.6% | Y 27.8% | T 14.4% | D 10.2% | S 9.2% | F 2.6% | |
| 118 E | E 92.2% | D 2.6% | I 2.0% | A 1.7% | | | |
| 125 F | F 79.4% | Y 11.8% | M 7.3% | L 1.5% | | | |
| 129 W | E 91.3% | S 8.6% | | | | | |
| 168 V | D 98.1% | A 1.0% | | | | | |
| 170 A | A 78.7% | S 17.6% | D 3.7% | | | | |

A triple mutant was found that improved enzyme function by 35 fold in only a single round of screening (see FIG. 4). This mutant (Y105Q, N136D, N170L) survived at 50 μg/ml cefotaxime.

Example 2

Secondary Library Generation of a Xylanase

PDA Pre-Screening Leads to Enormous Reduction in Number of Possible Sequences

To demonstrate that computational pre-screening is feasible and will lead to a significant reduction in the number of sequences that have to be experimentally screened, initial calculations for the B. circulans xylanase with and without the substrate were performed. The PDB structure 1 XNB of B. circulans xylanase and 1 BCX for the enzyme substrate complex were used. 27 residues inside the binding site were visually identified as belonging to the active site. 8 of these residues were regarded as absolutely essential for the enzy- If we consider all the amino acids obtained from the PDA calculation, including those with probabilities less than 1%, we obtain $4.1\times10^{15}$ different amino acid sequences. This is a reduction by 7 orders of magnitude. If one only considers those amino acids that have at least a probability of more than 1% as shown in Table 1 (1% criterion), the problem is decreased to $3.3\times10^9$ sequences. If one neglects all amino acids with a probability of less than 5% (5% criterion) there are only $4.0\times10^6$ sequences left. This is a number that can be easily handled by screening and gene shuffling techniques. Increasing the list of low energy sequences to 100,000 does not change these numbers significantly and the effect on the amino acids obtained at each position is negligible. Changes occur only among the amino acids with a probability of less than 1%.

Including the substrate in the PDA calculation further reduced the number of amino acids found at each position. If we consider those amino acids with a probability higher than 5%, we obtain $2.4\times10^6$ sequences (see Table 2).

TABLE 2

Probability of amino acids at the designed positions resulting from the PDA calculation of the enzyme substrate complex. Only those amino acids with a probability greater than 1% are shown.

| WT | PDA Probability Distribution | | | | | |
|---|---|---|---|---|---|---|
| 5 Y   | Y 69.2% | W 17.0% | H 7.3%  | F 6.0% | | |
| 7 Q   | Q 78.1% | E 18.0% | L 3.9%  | | | |
| 11 D  | D 97.1% | | | | | |
| 37 V  | V 50.9% | D 33.9% | S 5.4%  | A 1.2% | L 1.0% | |
| 39 G  | S 80.6% | A 19.4% | | | | |
| 63 N  | W 92.2% | D 3.9%  | Q 2.9%  | | | |
| 65 Y  | E 91.1% | L 8.7%  | | | | |
| 67 T  | E 92.8% | L 5.2%  | | | | |
| 71 W  | W 62.6% | E 13.3% | M 11.0% | S 6.9% | D 4.0% | |
| 80 Y  | M 66.4% | F 13.6% | E 10.7% | I 6.0% | L 1.3% | |
| 82 V  | V 86.0% | D 12.8% | | | | |
| 88 Y  | W 55.1% | Y 15.9% | N 11.4% | F 9.5% | K 1.9% | Q 1.4% D 1.4% M 1.4% |
| 110 T | D 99.9% | | | | | |
| 115 A | D 46.1% | S 27.8% | T 17.1% | A 7.9% | | |
| 118 E | I 47.6% | D 43.0% | E 3.6%  | V 2.5% | A 1.4% | |
| 125 F | Y 51.1% | F 43.3% | L 3.4%  | M 2.0% | | |
| 129 W | L 63.2% | M 28.1% | E 7.5%  | | | |
| 168 V | D 98.2% | | | | | |
| 170 A | T 92.3% | A 5.9%  | | | | |

These preliminary calculations show that PDA can significantly reduce the dimensionality of the problem and can bring it into the scope of gene shuffling and screening techniques (see FIG. 3).

We claim:

1. A method for generating at least one non-naturally occurring variant protein with at least one desired characteristic relative to a target protein comprising:
   a) inputting the coordinates of said target protein into a computer;
   b) identifying a list of variable residue positions in said target protein;
   c) applying at least one scoring function to said variable positions to generate a first set of amino acid residues at each of said variable positions to generate a primary library comprising optimized variant protein sequences;
   d) identifying a set of amino acids at each of said variable residue positions in said variant protein sequences of said primary library by generating a probability distribution table of said first set;
   e) recombining non-variable positions and variable residue positions of said second set to generate a secondary library of protein sequences, wherein the set of amino acids at each of said variable residue positions is used to generate the library of protein sequences, and wherein at least one member of said secondary library is not found in said primary library;
   f) synthesizing a plurality of said secondary library protein sequences and screening said sequences to identify at least one non-naturally occurring variant protein with at least one desired characteristic.

2. A method according to claim 1 wherein said recombining comprises:
   i) generating a set of oligonucleotide probes each encoding at least one of said variant amino acid residues;
   ii) using said probes in a polymerase chain reaction (PCR) to generate a plurality of oligonucleotide sequences, each encoding at least one of said second set of variant sequences; and,
   iii) producing said secondary library in host cells transformed with said oligonucleotide sequences.

3. A method according to claim 1, wherein said scoring function is a van der Waals potential scoring function.

4. A method according to claim 1, wherein said scoring function is a hydrogen bond potential scaring function.

5. A method according to claim 1, wherein said scoring function is an atomic solvation scoring function.

6. A method according to claim 1, wherein said scoring function is an electrostatic scoring function.

7. A method according to claim 1, wherein said scoring function is a secondary structure propensity scoring function.

8. A method according to claim 1 wherein said step c) comprises a plurality of scoring functions.

9. A method according to claim 8 wherein said plurality of scoring functions includes a van der Waals potential scoring function.

10. A method according to claim 8 wherein said plurality of scoring functions includes a hydrogen bond potential scoring function.

11. A method according to claim 8 wherein said plurality of scoring functions includes an atomic solvation scoring function.

12. A method according to claim 8 wherein said plurality of scoring functions includes an electrostatic scoring function.

13. A method according to claim 8 wherein said plurality of scoring functions includes a secondary structure propensity scoring function.

14. A method according to claim 1 wherein said step c) utilizes Protein Design Automation to computationally generate said optimized primary variant sequences.

15. A method according to any of claims 1-14 wherein said recombining is done computationally.

16. A method according to any of claims 1-14 wherein said recombining is done by using gene shuffling.

17. A method according to any of claims 1-14 wherein said recombining is done by using multiple PCR with pooled oligonucleotides.

18. A method according to claim 1 wherein said screening is done using a plurality of synthesized genes encoding a plurality of said variant proteins.

* * * * *